(12) United States Patent
Klinman et al.

(10) Patent No.: US 7,892,569 B2
(45) Date of Patent: Feb. 22, 2011

(54) METHODS OF ALTERING AN IMMUNE RESPONSE INDUCED BY CPG OLIGODEOXYNUCLEOTIDES

(75) Inventors: Dennis M. Klinman, Potomac, MD (US); Mayda Gursel, Ankara (TR); Ihsan Gursel, Ankara (TR)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 78 days.

(21) Appl. No.: 12/065,085

(22) PCT Filed: Aug. 28, 2006

(86) PCT No.: PCT/US2006/033774
§ 371 (c)(1),
(2), (4) Date: Feb. 27, 2008

(87) PCT Pub. No.: WO2007/027718
PCT Pub. Date: Mar. 8, 2007

(65) Prior Publication Data
US 2008/0249056 A1      Oct. 9, 2008

Related U.S. Application Data

(60) Provisional application No. 60/713,547, filed on Aug. 31, 2005, provisional application No. 60/713,349, filed on Aug. 31, 2005.

(51) Int. Cl.
*A61K 45/00*    (2006.01)
(52) U.S. Cl. .............. 424/278.1; 424/130.1; 424/184.1; 514/44
(58) Field of Classification Search ........................ None
See application file for complete search history.

(56) References Cited

FOREIGN PATENT DOCUMENTS

| WO | WO 99/56755 | 11/1999 |
| WO | WO 00/61151 | 10/2000 |
| WO | WO 01/22990 | 4/2001 |

OTHER PUBLICATIONS

Gough et al, The Journal of Immunology 172:3678-3685, 2004.*
Gijbels et al (J. Clin. Invest., 94:2177-82, 1994).*
Tobata et al (Journal of Leukocyte Biology 77:777-786, 2005.*
Gursel et al., "CXCL16 Influences the Nature and Specificity of CpG-Induced Immune Activation," *The Journal of Immunology*, 177: 1575-1580, 2006.
Abel et al., "The Transmembrane CXC-Chemokine Ligand 16 is Induced by IFN-γ and TNF-α and Shed by the Activity of the Disintergrin-Like Metalloproteinase ADAM10," *Journal of Immunology*, 172(10):6362-6372 (May 15, 2004).
Gursel et al., "CXCL16 Influences the Nature and Specifically of CpG-Induced Immune Activation," *Journal of Immunology*, 177(3):1575-1580 (Aug. 3, 2006).
Verthelyi et al., "Human Peripheral Blood Cells Differentially Recognize and Respond to Two Distinct CPG Motifs," *Journal of Immunology*, 166(4):2372-2377 (Feb. 15, 2001).
International Search report from PCT Application No. PCT/US2006/033774, dated Feb. 5, 2007.

* cited by examiner

*Primary Examiner*—Patricia A Duffy
(74) *Attorney, Agent, or Firm*—Klarquist Sparkman, LLP

(57) ABSTRACT

It is disclosed herein that agents that affect the activity and/or expression of CXCL16 can be used to alter the uptake of D-type CpG oligodeoxynucleotides (D ODNs). Methods of inducing an immune response are disclosed that include administering agents that increase the activity and/or expression of CXCL16 and a D ODN. Methods of decreasing an immune response to a CpG ODN are also disclosed. These methods include administering an agent that decreases the activity and/or expression of CXCL16. Compositions including one or more D-type ODNs and an agent that modulates that activity and/or expression of CXCL16 are provided.

26 Claims, 7 Drawing Sheets

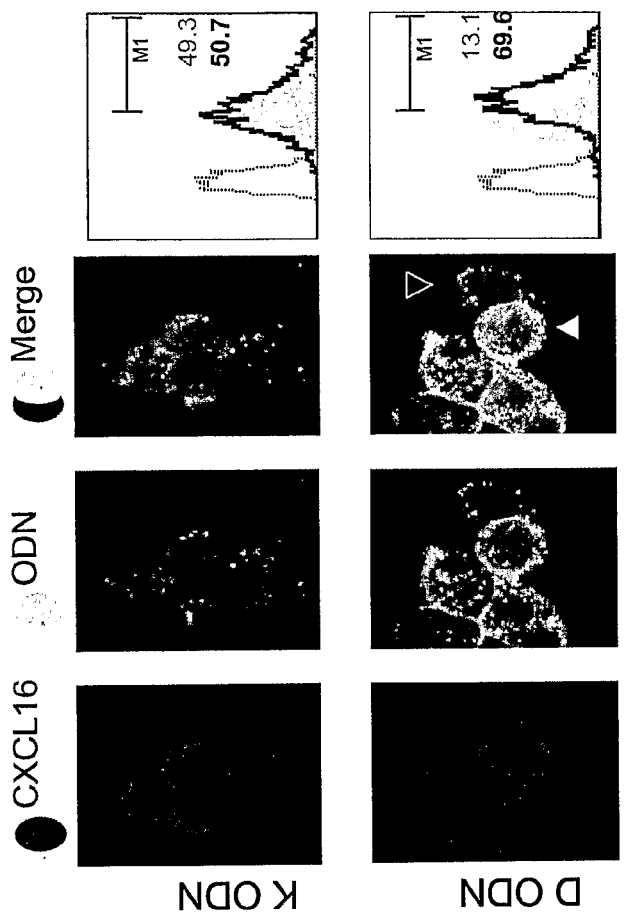
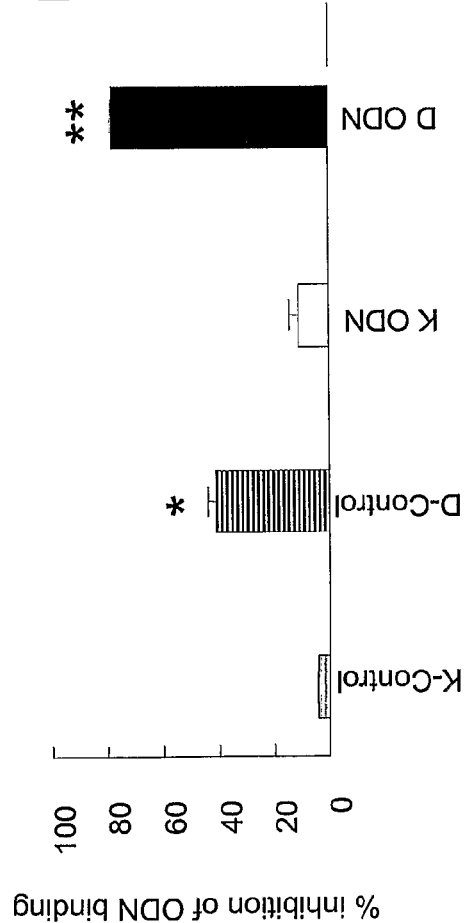
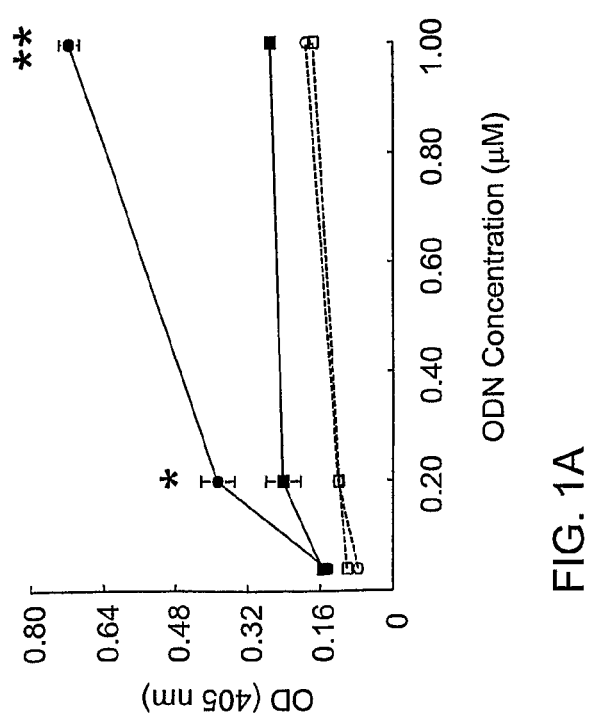
FIG. 1A
FIG. 1B
FIG. 1C

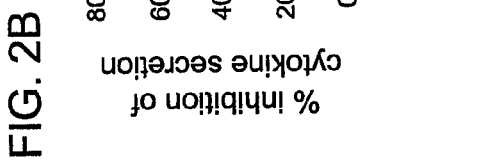
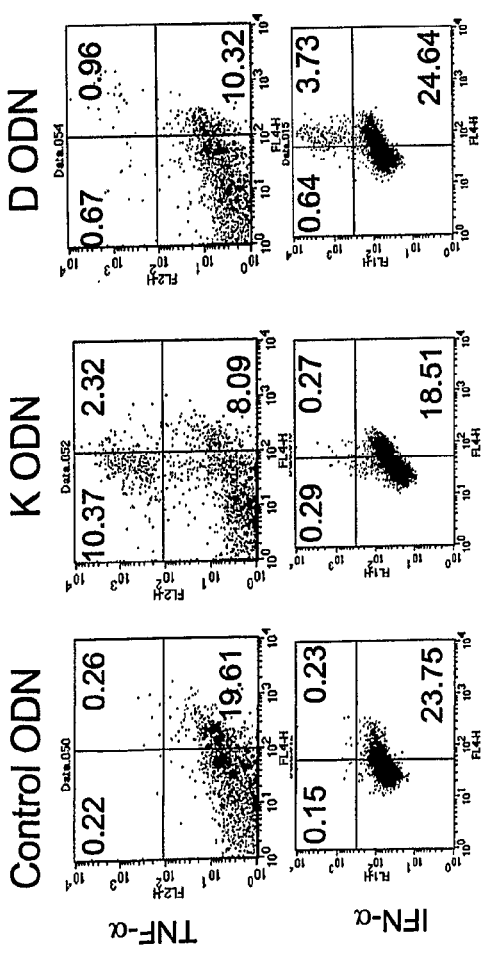
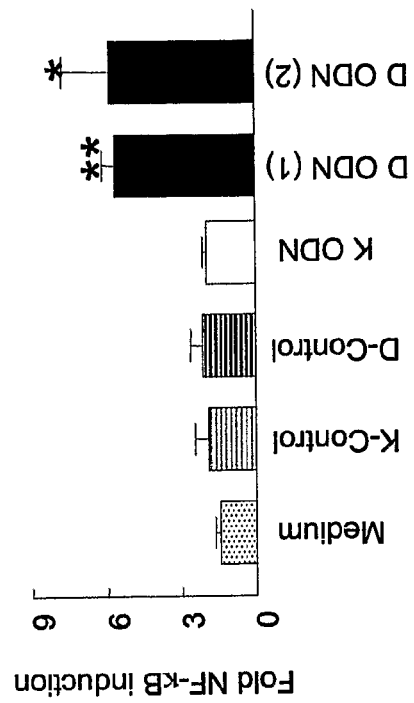
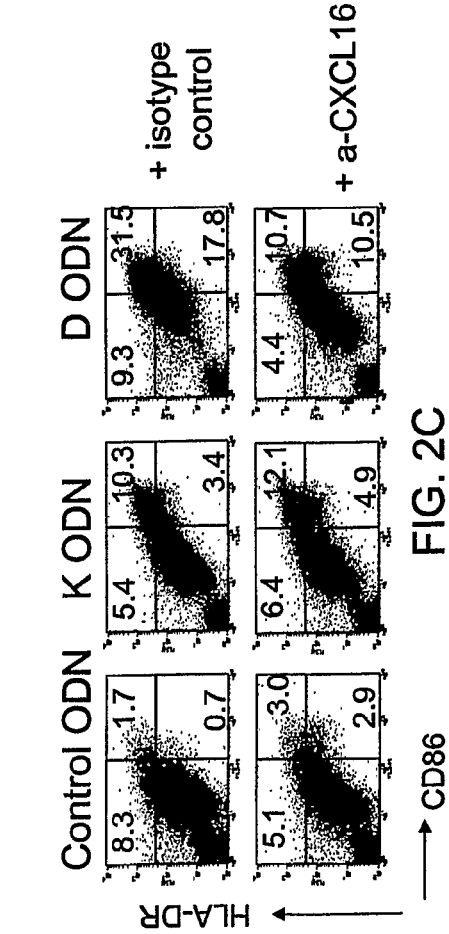
FIG. 2A
FIG. 2B
FIG. 2C
FIG. 2D

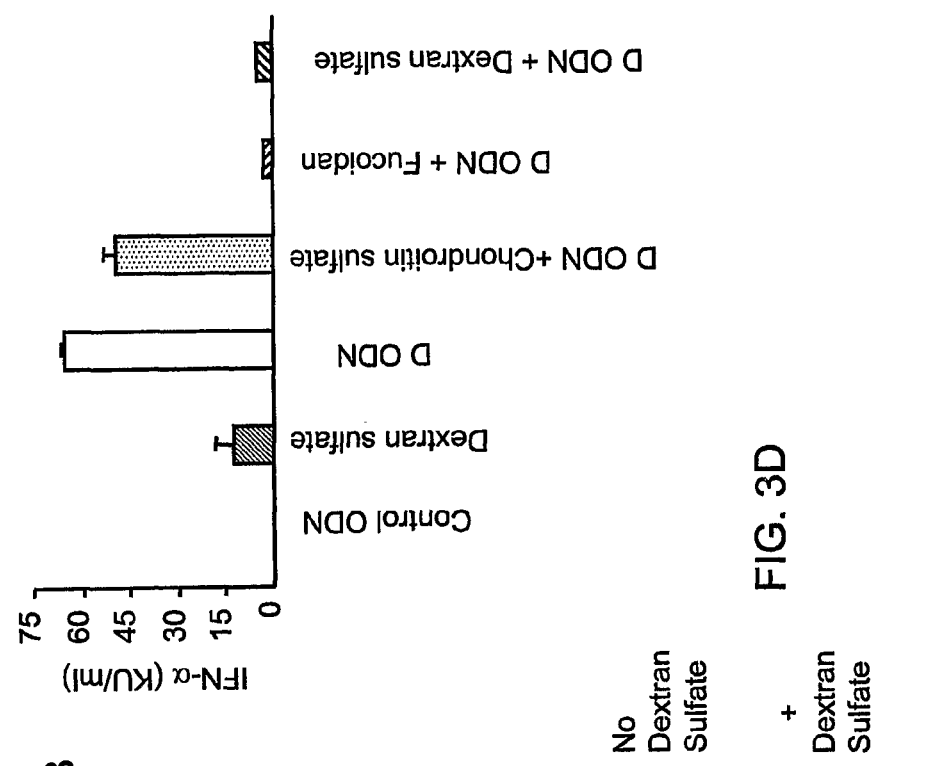
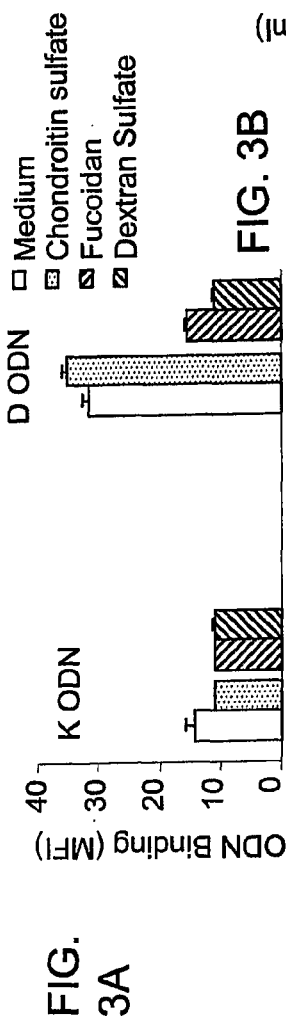
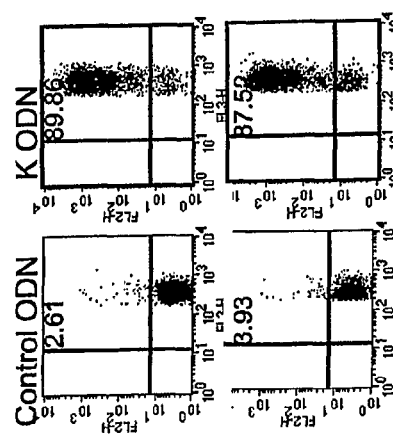
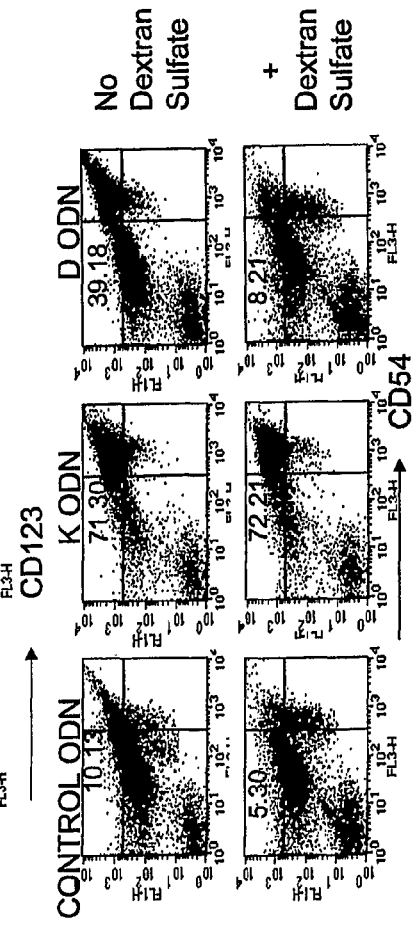
FIG. 3A
FIG. 3B
FIG. 3C
FIG. 3D

FIG. 5
CXCL16 positive pDC
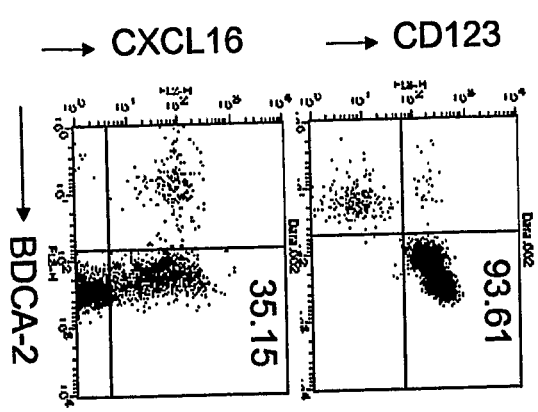
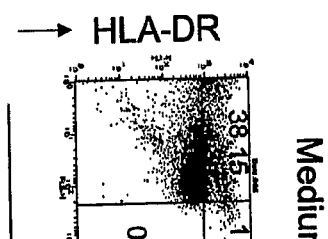
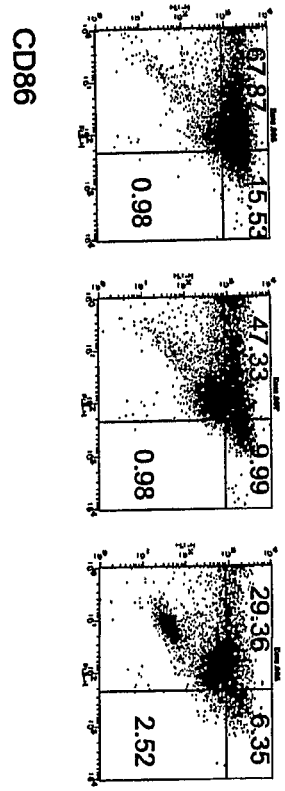
CXCL16 negative pDC
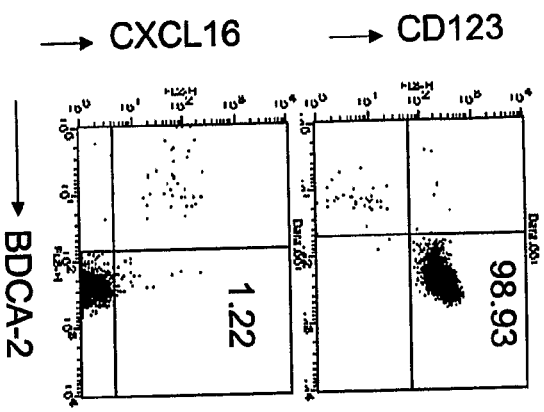
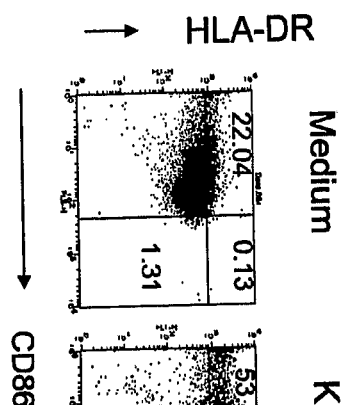
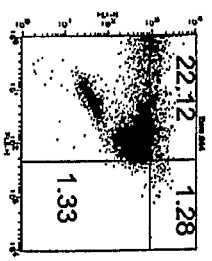

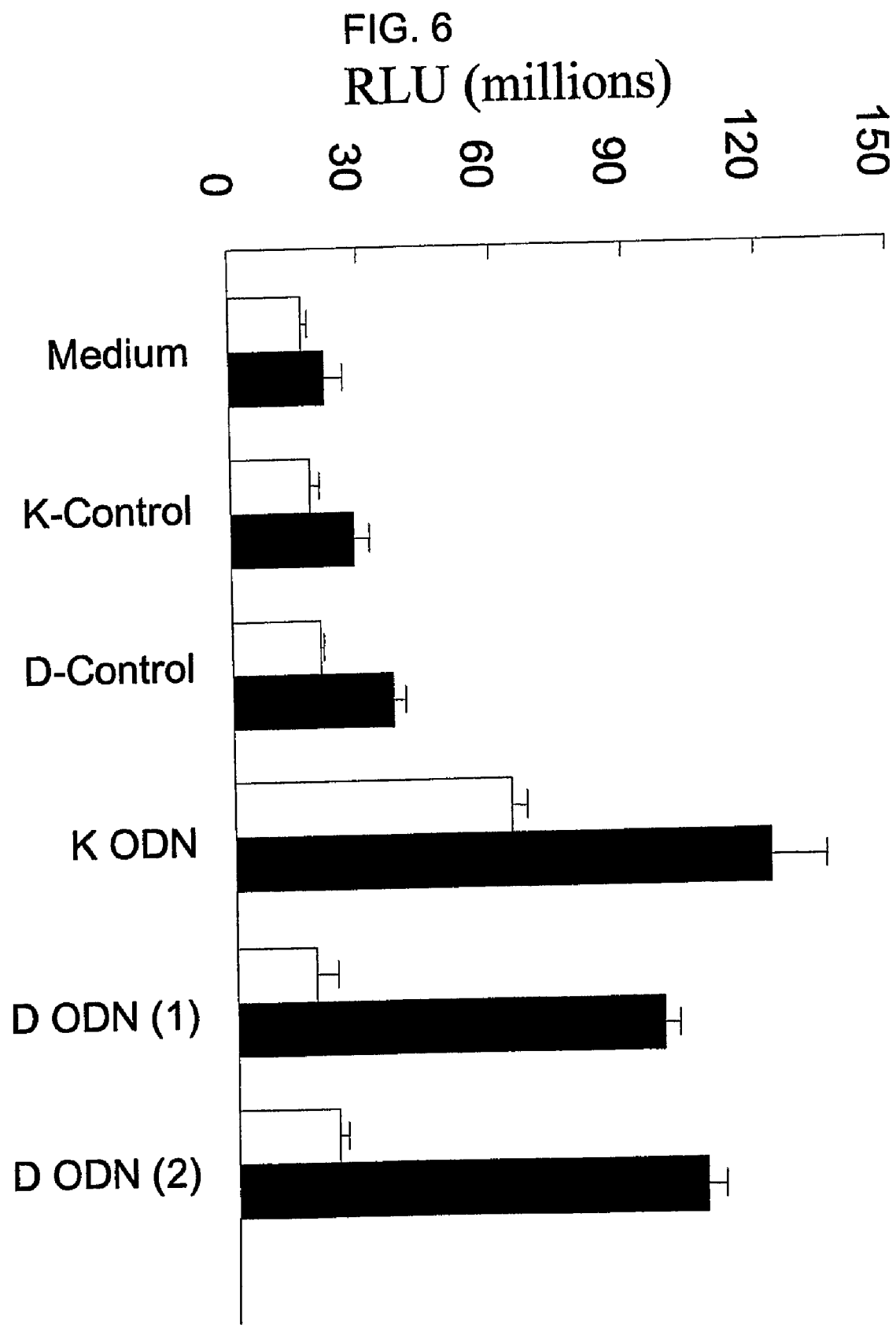

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 1
ggtgcatcga tgcaggggggg    20

<210> SEQ ID NO 2
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 2
ggtgcaccgg tgcaggggggg    20

<210> SEQ ID NO 3
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 3
ggtgcgtcga tgcaggggggg    20

<210> SEQ ID NO 4
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 4
ggtgtgtcga tgcaggggggg    20

<210> SEQ ID NO 5
<211> LENGTH: 18
<212> TYPE: DNA
<213> ORGANISM: Artificial sequence
<220> FEATURE:
<223> OTHER INFORMATION: D type synthetic oligodeoxynucleotide

<400> SEQUENCE: 5
tgcatcgatg caggggggg    18

<210> SEQ ID NO 6
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 6
ggtgcatcga tacaggggggg    20

```
<210> SEQ ID NO 7
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 7
ggtgcatcga tgcagggggg                                              20

<210> SEQ ID NO 8
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 8
ggtgcatcgt tgcagggggg                                              20

<210> SEQ ID NO 9
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 9
ggtgcgtcga cgcagggggg                                              20

<210> SEQ ID NO 10
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 10
ggtcgatcga tgcacggggg                                              20

<210> SEQ ID NO 11
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 11
ggtgcatcga tgcagggggg                                              20

<210> SEQ ID NO 12
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 12
ggtgcatcga cgcagggggg                                              20

<210> SEQ ID NO 13
<211> LENGTH: 20
<212> TYPE: DNA
<213> ORGANISM: Artificial sequence
<220> FEATURE:
<223> OTHER INFORMATION: D type synthetic oligodeoxynucleotide
```

```
<400> SEQUENCE: 13
ggtgcatcga taggcgggggg                                              20

<210> SEQ ID NO 14
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 14
ggtgcaccga tgcagggggg                                              20

<210> SEQ ID NO 15
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 15
cctgcatcga tgcagggggg                                              20

<210> SEQ ID NO 16
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 16
ggtatatcga tataggggggg                                             20

<210> SEQ ID NO 17
<211> LENGTH: 20
<212> TYPE: DNA
<213> ORGANISM: Artificial sequence
<220> FEATURE:
<223> OTHER INFORMATION: D type synthetic oligodeoxynucleotide

<400> SEQUENCE: 17
ggtggatcga tccagggggg                                              20

<210> SEQ ID NO 18
<211> LENGTH: 21
<212> TYPE: DNA
<213> ORGANISM: Artificial sequence
<220> FEATURE:
<223> OTHER INFORMATION: CXCL16 forward primer; synthetic
      oligonucleotide

<400> SEQUENCE: 18
gagctcactc gtcccaatga a                                            21

<210> SEQ ID NO 19
<211> LENGTH: 19
<212> TYPE: DNA
<213> ORGANISM: Artificial sequence
<220> FEATURE:
<223> OTHER INFORMATION: CXCL16 reverse primer; synthetic
      oligonucleotide

<400> SEQUENCE: 19
tcaggcccaa ctgccagac                                               19
```

```
<210> SEQ ID NO 20
<211> LENGTH: 22
<212> TYPE: DNA
<213> ORGANISM: Artificial sequence
<220> FEATURE:
<223> OTHER INFORMATION: CXCL16 probe; synthetic oligonucleotide

<400> SEQUENCE: 20
caccattcac actgcgggcc ac                                             22

<210> SEQ ID NO 21
<211> LENGTH: 32
<212> TYPE: DNA
<213> ORGANISM: Artificial sequence
<220> FEATURE:
<223> OTHER INFORMATION: D type consensus oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (4)..(4)
<223> OTHER INFORMATION: n is a or g
<220> FEATURE:
<221> NAME/KEY: misc_feature
<222> LOCATION: (5)..(5)
<223> OTHER INFORMATION: n is c or t
<220> FEATURE:
<221> NAME/KEY: misc_feature
<222> LOCATION: (8)..(8)
<223> OTHER INFORMATION: n is a or g
<220> FEATURE:
<221> NAME/KEY: misc_feature
<222> LOCATION: (9)..(9)
<223> OTHER INFORMATION: n is c or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (13)..(22)
<223> OTHER INFORMATION: n is a, c, g, or t
<220> FEATURE:
<221> NAME/KEY: repeat_unit
<222> LOCATION: (13)..(22)
<223> OTHER INFORMATION: Any one or all of nucleotides 13 through 22
      can either be present or absent.
<220> FEATURE:
<221> NAME/KEY: misc_feature
<222> LOCATION: (27)..(32)
<223> OTHER INFORMATION: n is g
<220> FEATURE:
<221> NAME/KEY: repeat_unit
<222> LOCATION: (27)..(32)
<223> OTHER INFORMATION: Any one or all of nucleotides 27 through 32
      can either be present or absent.

<400> SEQUENCE: 21
nnnnncgnnn nnnnnnnnnn nngggnnnn nn                                   32

<210> SEQ ID NO 22
<211> LENGTH: 10
<212> TYPE: DNA
<213> ORGANISM: Artificial sequence
<220> FEATURE:
<223> OTHER INFORMATION: K type consensus oligodeoxynucleotide
<220> FEATURE:
<221> NAME/KEY: misc_feature
<222> LOCATION: (1)..(3)
<223> OTHER INFORMATION: n is a, c, g, or t
```

```
-continued

<220> FEATURE:
<221> NAME/KEY: misc_feature
<222> LOCATION: (4)..(4)
<223> OTHER INFORMATION: n is a, g, or t
<220> FEATURE:
<221> NAME/KEY: misc_feature
<222> LOCATION: (7)..(7)
<223> OTHER INFORMATION: n is a or t
<220> FEATURE:
<221> NAME/KEY: misc_feature
<222> LOCATION: (8)..(10)
<223> OTHER INFORMATION: n is a, c, g, or t

<400> SEQUENCE: 22 nnnncgnnnn                                                                    10
```

METHODS OF ALTERING AN IMMUNE RESPONSE INDUCED BY CPG OLIGODEOXYNUCLEOTIDES

CROSS REFERENCE TO RELATED APPLICATIONS

This is the U.S. National Stage of International Application No. PCT/US2006/033774, filed Aug. 28, 2006, which was published in English under PCT Article 21(2), which in turn claims the benefit of U.S. Provisional Application No. 60/713,547, filed Aug. 31, 2005, which is incorporated herein by reference in its entirety.

PRIORITY CLAIM

This claims the benefit of U.S. Provisional Application No. 60/713,349, filed Aug. 31, 2005, which is incorporated herein by reference in its entirety.

FIELD

This application relates to the field of immunology, specifically to agents that can be used to alter the uptake of immunostimulatory oligodeoxynucleotides (ODNs).

BACKGROUND

DNA is a complex macromolecule whose activities are influenced by its base composition and base modification, as well as helical orientation. Bacterial DNA, as well as certain synthetic oligodeoxynucleotides (ODNs) containing unmethylated CpG sequences, can induce proliferation and immunoglobulin production by murine B cells. Unmethylated CpG dinucleotides are more frequent in the genomes of bacteria and viruses than vertebrates. Studies have suggested that immune recognition of these motifs may contribute to the host's innate immune response. (Klinman et al., *Proc. Natl. Acad. Sci. USA* 93:2879, 1996; Yi et al., *J. Immun.* 157:5394, 1996; Liang et al., *J. Clin. Invest.* II 9:89, 1996; Krieg et al., *Nature* 374:546, 1995).

A CpG oligodeoxynucleotide (ODN) is an oligodeoxynucleotide including a CpG motif, wherein the pyrimidine ring of the cytosine is unmethylated. Three types of CpG ODNs have been identified: C-type, K-type and D-type ODNs. Generally, CpG ODNs range from about 8 to 30 bases in size. D- and K-type nucleic acid sequences have been described in the published PCT Publication No. WO 98/18810A1 (K-type) and published PCT Publication No. WO 00/61151 (D-type). Generally D ODNs can stimulate a cellular immune response, while K ODNs can stimulate a humoral immune response.

Unmethylated CpG motifs, including both D-type ODNs and K-type ODNs, are recognized by the Toll-like receptor 9 (TLR9) expressed on immune cells (such as B cells, macrophages, and dendritic cells). The CpG DNA is taken up by an endocytic/phagocytic pathway. It is known that the interaction of CpG ODN with TLR9 triggers recruitment of a MyD88 adaptor molecule, activation of an IL-1R kinase-1 and other factors, resulting in the production of cytokines (see Latz et al., *Nat. Immunol.* 5:190-8, 2004).

CpG ODNs can be used to induce an immune response. Thus, they have been found to have many uses, such as to induce an immune response to antigens, in the production of vaccines, and as adjuvants. It would be advantageous to be able to alter the uptake of CpG ODN by cells, in order to alter the immune response produced by these oligonucleotides. Methods to alter the uptake and subsequent immune activation triggered by CpG ODN are disclosed herein.

SUMMARY

It is disclosed herein that agents that affect the activity and/or expression of CXCL16 can be used to alter the uptake of CpG oligodeoxynucleotides (ODN), specifically D-type CpG oligodeoxynucleotides (D ODN). Thus, agents that affect the activity and/or expression of CXCL16 can be used to alter an immune response induced by D ODN. In one example, the agent increases the activity and/or expression of CXCL16, thereby increasing the uptake of D ODN. Agents that increase the activity and/or expression of CXCL16 can be used to increase an immune response induced by a D ODN. Agents that decrease the activity and/or expression of CXCL16 can be used to decrease an immune response induced by D ODN.

Specific compositions including one or more D-type ODNs and an agent that modulates that activity and/or expression of CXCL16 are provided herein. These compositions are of use to induce an immune response, such as to a specific antigen.

The foregoing and other features and advantages will become more apparent from the following detailed description of several embodiments, which proceeds with reference to the accompanying figures.

BRIEF DESCRIPTION OF THE FIGURES

FIGS. 1A-1C are graphs and digital images illustrating that CXCL16 selectively recognizes D ODN. FIG. 1A is a line graph showing CpG ODN binding to recombinant CXCL16. 96-well flat bottom ELISA plates were coated with 0.4 µg/ml anti-CXCL16 antibody and then incubated without (dotted lines) or with 200 ng/ml of recombinant CXCL16 (full lines). Following washing, 1, 0.2 or 0.04 µM biotin-conjugated K or D oligodeoxynucleotide (ODN) were added. After washing, ODN binding was detected colorimetrically using phosphatase-conjugated avidin followed by a phosphatase specific colorimetric substrate. Results are presented as average±standard deviation (SD) of three independent readings. FIG. 1B is a set of digital images and plots showing that D but not K ODN colocalize with CXCL16 and its uptake is enhanced in transfected HEK293 cells. CXCL16 transfected HEK293 cells were incubated with 3 µM of FITC conjugated CpG ODN at 37° C. for 20 minutes. Cells were stained for CXCL16 expression (left) and colocalization (bright cells, right) with ODN (middle) was determined using confocal microscopy. Percent of FITC-ODN bright cells in mock transfected (filled histograms) and CXCL16 transfected (dark open histograms) was determined using flow cytometry and are shown against background staining (dotted histograms). Results are representative of at least six independent experiments. FIG. 1C is a bar graph showing that anti-CXCL16 inhibit D ODN binding to pDC. Binding of FITC conjugated ODN to CD123/BDCA-2 double positive pDC was determined in the absence or presence of anti-CXCL16 or isotype matched control (100 µg/ml each). Percent inhibition of uptake was determined comparative to the isotype matched control group. Results represent the mean±SD of 2 experiments (*, $P<0.05$; **, $P<0.01$).

FIGS. 2A-2D are graphs and plots showing that CXCL16 positive cells preferentially respond to D ODN. FIG. 2A is a plot showing that CXCL16 expression versus cytokine production in pDCs stimulated with CpG ODN. Peripheral blood mononuclear cells (PBMC) ($4 \times 10^6$/ml) were stimulated with Control, K or D ODN in the presence of Brefeldin A (10 µg/ml) for 4.5 h (TNF-α) or for 12 hours (Brefeldin A was added after 8 hours of incubation) in the case of IFN-α. Cytokine producing cells were assessed from the CD123+-gated cells as a function of CXCL16 expression. Results are representative of 3 independent experiments. FIG. 2B is a bar graph showing that antibodies against CXCL16 inhibit D ODN induced cytokine production. PBMC were preincubated with 25 µg/ml of isotype (open bars) or anti-CXCL16 antibody (filled bars) for 30 minutes at 37° C. and then stimulated with 1 µM each of K or with 3 µM D ODN for 24 hours. Percent inhibition of cytokine production was calculated from three different individuals (*, P<0.05). FIG. 2C is a plot showing the effect of anti-CXCL16 on the upregulation of HLA-DR and CD86 by CpG ODN. Elutriated monocytes were preincubated with anti-CXCL16 or isotype matched control antibody and then stimulated with Control (3 µM), K (1 µM) or D (3 µM) ODN for 24 hours. The percent of cells expressing HLA-DR and CD86 was determined by flow cytometry. Results are representative of five independent experiments. FIG. 2D is a bar graph of the results showing HEK293 cells transfected with CXCL16 gain responsiveness to D ODN. HEK293 cells stably expressing TLR9 were co-transfected with p5xNF-kB. In this figure, the ratio of NF-kB induction in CXCL16 transfected over mock transfected is displayed for each ODN. All ODN names are shown on the X-axis. B-luciferase plus control plasmid or CXCL16. Relative luciferase units from CXCL16 transfected cells over those from mock transfected cells were determined 24 hours after ODN treatment (3 µM). Results represent the mean±SD of 4 independent experiments (*, P<0.05; **, P<0.01).

FIGS. 3A-3D are bar graphs and plots showing the effect of scavenger receptor ligands on the binding and activity of CpG ODN. FIG. 3A is a bar graph of the results obtained when purified pDC were preincubated (20 minutes at 4° C.) with medium or with 50 µg/ml each of inhibitors followed by addition of 1 µM FITC conjugated ODN. Mean fluorescence intensity representing binding of FITC-ODN was assessed using flow cytometry. Results represent the mean±S.D of three independent experiments. FIG. 3B is a bar graph showing D ODN induced IFN-α from peripheral blood mononuclear cells (PBMC). Open bars: medium; dotted bars: chondroitin sulfate; right-striped bars: fucoidan; left-striped bars: dextran sulfate Production of IFN-α from PBMC (in the absence or presence of 50 µg/ml inhibitors) was determined by ELISA from 24 hour culture supernatants. FIG. 3C is a plot showing K ODN induced TNF-α production in pDC (in the absence or presence of 50 µg/ml dextran sulfate). TNF-α production was determined using intracytoplasmic cytokine staining (representative plots of three independent experiments). FIG. 3D is a plot showing the results obtained when purified pDC were incubated with 1 µM each of K or with 3 µM D ODN in the absence or presence of 50 µg/ml dextran sulfate. Upregulation of HLA-DR/CD54 was determined 24 hours later using flow cytometry.

FIG. 4A shows pDCs express CXCL16 on their surface. pDCs were enriched from PBMC using the BDCA-4 magnetic cell separation kit. Expression of CXCL16 versus isotype matched control was analyzed on CD123/BDCA-2 double positive cells. Data is representative of at least five independent experiments. FIG. 4B is a plot showing that anti-CXCL16 specifically inhibits binding of D ODN to pDC. Binding of FITC conjugated D ODN to CD123 gated cells was analyzed using flow cytometry. The figure shows that both basophils (BDCA-2$^{negative}$) and pDCs (BDCA-2$^{positive}$) bind D ODN in the presence of isotype matched antibody and that only binding to the pDC but not to the basophil population (which do not express CXCL16) is inhibited by anti-CXCL16, providing evidence for the specificity of this antibody.

FIG. 5 is a set of plots of the results obtained when elutriated monocytes were stained for pDC markers and CXCL16 and BDCA-2/CD123 gated cells were sorted into the CXCL16 negative or CXCL16 positive+negative populations using FACSAria cell sorter. The resulting populations were then incubated with 1 and 3 µM of K and D ODN, respectively, or with 1×10$^7$ pfu/ml of UV-inactivated HSV-1. Twenty-four hours later, cells were stained and expression of HLA-DR/CD86 was assessed by flow cytometry.

FIG. 6 is a bar graph showing the expression of CXCL16 in HEK293 cells stably expressing TLR9 confers D ODN responsiveness. Stable TLR9 expressing HEK293 cells were co-transfected with 0.5 µg p5xNF-kB B-luc and 1 µg of CXCL16 or control plasmid for 24 hours. Data show relative luciferase units obtained following 24 hours incubation with 3 µM ODN in mock transfected (open bars) and CXCL16 (filled bars) transfected TLR9 expressing HEK293 cells.

SEQUENCE LISTING

Figure 4A:
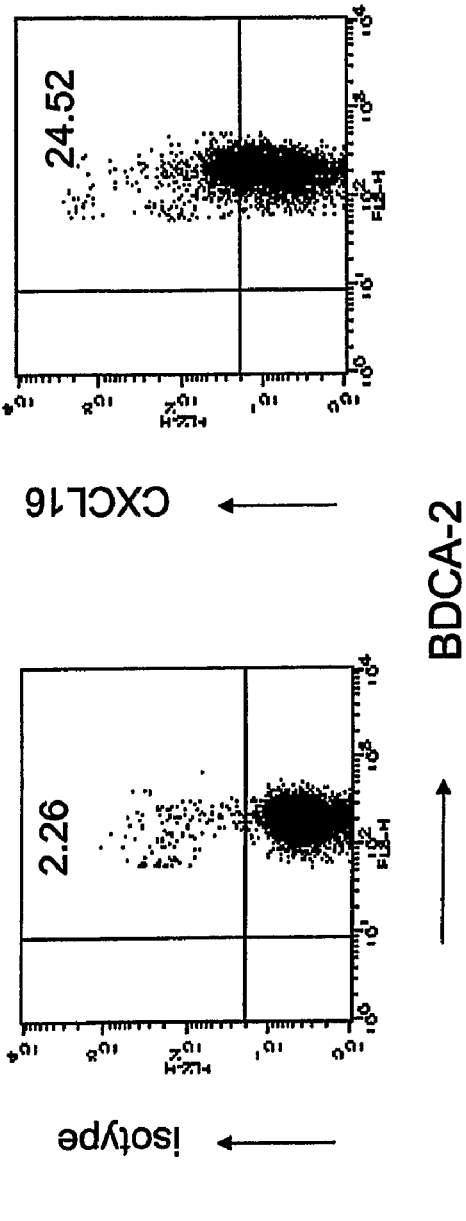
FIGS. 4A-4B are plots showing the expression of CXCL16.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand where appropriate.

SEQ ID NOs: 1-17 are the nucleic acid sequences of D ODN.

SEQ ID NOs: 18-20 are the nucleic acid sequences of CXCL16 probes and primers.

SEQ ID NO: 21 is the consensus nucleic acid sequence of a D ODN.

SEQ ID NO: 22 is the consensus nucleic aid sequence of a K ODN.

DETAILED DESCRIPTION

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

ADAM-10: A protein that is an enzyme also known as disintegrin, metalloprotease domain 10, and MADM mammalian disintegrin metalloprotease. It is a member of the ADAM protein family. The protein has been shown to be a physiologically relevant TNF-processing enzyme (TNF-alpha convertase, TNF-alpha converting enzyme). It cleaves the 26 kDa membrane-bound precursor form of TNF-alpha to release the soluble mature 17 kDa TNF form.

ADAM-10 contains the canonical zinc metalloproteinase motif, and has been shown to be proteolytically active. ADAM-10 from bovine kidney was shown to have type-IV collagenolytic activity, making ADAM-10 a "gelatinase." ADAM-10 is efficiently inhibited by the endogenous MMP inhibitors TIMP-1 and TIMP-3, but not by TIMP-2 and TIMP-4.

The full length ADAM-10 sequence codes for a 748 amino acid protein, with a predicted mass, is 84.142 kD. Glycosylation and the cyteine-rich regions make the protein run at 98 kD on reduced SDS PAGE, and 60-58 kD when Furin processed. A smaller 691 amino acid sequence for ADAM-10, lacking the transmembrane domain, has been reported, with a predicted molecular weight of 77.633 kD. ADAM-10 is thought to be membrane-anchored under normal conditions. The sequence of ADAM-10 can be found, for example, as GENBANK™ Accession Nos. AAC51766 (Sep. 26, 1997), AF009615 (Sep. 27, 1997) and CAA88463 (Apr. 18, 2005, MADAM), which are all incorporated herein by reference.

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes.

"C" class oligodeoxynucleotides (ODNs): ODNs that resemble K ODNs and are composed of only phosphorothiote nucleotides. Typically, C class ODNs have a TCGTCG motif at the 5' end and have a CpG motif imbedded in a palindromic sequence. Backbone modifications like 2'-O-methyl modifications especially in the 5' part of the ODN influence IFN-alpha-producing capacity of these ODN. C class ODNs have combined properties of D- and K-type ODNs. This class of ODNs stimulates B cells to secrete IL-6 and stimulates plasmacytoid dendritic cells to produce interferon-α C class ODNs also induce IP-10 production and strong NK activation.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligonucleotides include both D- and K-type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cancer: A malignant neoplasm that has undergone characteristic anaplasia with loss of differentiation, increased rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived.

Chemotherapy or chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., ©2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic.

CXCL16: A chemokine that specifically binds to the CXCL16 receptor (CXCR6, also known as Bonzo), also known as SR-PSOX. Exemplary amino acid sequences for CXCL16, and nucleotide sequence(s) encoding CXCL16 are set forth as GENBANK™/EMBL Data Bank as Accession Nos. AF275260 (human SR-PSOX, Jan. 2, 2001), AF277001 (murine SR-PSOX, Jan. 8, 2001), and AF277000 (porcine SR-PSOX, Jan. 8, 2001), which are all incorporated herein by reference). Variants of CXCL16 that bind to their receptor are also encompassed by this disclosure. The CXCL16 receptor is a type I membrane protein which is expressed on macrophages and dendritic cells and has a molecular weight of approximately 30 KDa.

CXCL16 is a ligand for the CXC-chemokine receptor CXCR6, and is a scavenger receptor for oxidized low density lipoprotein (LDL). CXCL16 is expressed on the cell membrane as a multidomain molecule including a chemokine domain followed by a glycosylated mucin-like stalk and single transmembrane helix followed by a short cytoplasmic tail. CXCL16 is expressed on antigen presenting cells (APCs). CXCL16 induces chemotaxis of activated T cells and bone marrow plasma cells. Cell expressed CXCL16 is released from the cell membrane by proteolytic cleavage. The disintegrin-like metalloproteinase ADAM-10 plays a role in CXCL16 cleavage. CXCL16 is induced by IFN-γ and TNF-α.

Cytokine: Proteins made by cells that affect the behavior of other cells, such as lymphocytes. In one embodiment, a cytokine is a chemokine, a molecule that affects cellular trafficking.

D-Type Oligodeoxynucleotide (D ODN): An oligodeoxynucleotide including an unmethylated CpG motif that has a sequence represented by the formula:

wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D-type ODN is at least about 16 nucleotides in length and includes a sequence represented by the formula:

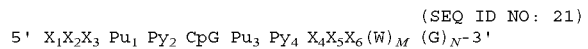

(SEQ ID NO: 21)

wherein the central CpG motif is unmethylated, Pu is a purine nucleotide, Py is a pyrimidine nucleotide, X and W are any nucleotide, M is any integer from 0 to 10, and N is any integer from 4 to 10. An additional detailed description of D ODN sequences and their activities can be found in Verthelyi et al., J. Immunol. 166:2372-2377, 2001, which is herein incorporated by reference. Generally D ODNs can stimulate a cellular response. For example, an "effective amount" or "therapeutically effective amount" of a D ODN is an amount of the D ODN sufficient to stimulate a response.

Epitope: An antigenic determinant. These are particular chemical groups or peptide sequences on a molecule that are antigenic, i.e. that elicit a specific immune response. An antibody binds a particular antigenic epitope.

Functionally equivalent: Sequence alterations, for example in a D-type ODN, that yield the same results as described herein. Such sequence alterations can include, but are not limited to, deletions, base modifications, mutations, labeling, and insertions.

Immune response: A response of a cell of the immune system, such as a B cell, or a T cell, to a stimulus. In one embodiment, the response is specific for a particular antigen (an "antigen-specific response").

A "parameter of an immune response" is any particular measurable aspect of an immune response, including, but not limited to, cytokine secretion (IL-6, IL-10, IFN-α, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. One specific, non-limiting example of a statistical test used to assess a substantial increase is the use of a Z test to compare the percent of samples that respond to a D ODN as compared to the percent of samples that respond to a control. A non-parametric ANOVA can be used to compare differences in the magnitude of the response induced by D ODN as compared to the percent of samples that respond using a control. In this example, $p \leq 0.05$ is significant, and indicates a substantial increase in the parameter of the immune response. One of skill in the art can readily identify other statistical assays of use.

Infectious agent: An agent that can infect a subject, including, but not limited to, viruses, bacteria, and fungi.

Examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of Hepatitis B virus), the agents of non-A, non-B Hepatitis (class 1=internally transmitted; class 2=parenterally transmitted (i.e., Hepatitis C); Norwalk and related viruses, and astroviruses).

Examples of infectious bacteria include: *Helicobacter pyloris; Borelia burgdorferi; Legionella pneumophilia; Mycobacteria* sps (such as. *M. tuberculosis, M. avium, M. intracellulare, M. kansaii, M. gordonae*); *Staphylococcus aureus, Neisseria gonorrhoeae; Neisseria meningitidis; Listeria monocytogenes; Streptococcus pyogenes* (Group A *Streptococcus*); *Streptococcus agalactiae* (Group B *Streptococcus*); *Streptococcus* (viridans group); *Streptococcus faecalis; Streptococcus bovis; Streptococcus (anaerobic* sps); *Streptococcus pneumoniae*; pathogenic *Campylobacter* sp.; *Enterococcus* sp.; *Haemophilus influenzae; Bacillus antracis; corynebacterium diphtheriae; corynebacterium* sp.; *Erysipelothrix rhusiopathiae; Clostridium perfringers; Clostridium tetani; Enterobacter aerogenes; Klebsiella pneumoniae; Pasturella multocida; Bacteroides* sp.; *Fusobacterium nucleatum; Streptobacillus moniliformis; Treponema pallidum; Treponema pertenue; Leptospira*; and *Actinomyces israelli*.

Examples of infectious fungi include, but are not limited to, *Cryptococcus neoformans; Histoplasma capsulatum; Coccidioides immitis; Blastomyces dermatitidis; Chlamydia trachomatis*; and *Candida albicans*.

Other infectious organisms (such as protists) include: *Plasmodium falciparum* and *Toxoplasma gondii*.

Interferon alpha (α): IFN-α forms are produced by monocytes/macrophages, lymphoblastoid cells, fibroblasts, and a number of different cell types following induction by viruses, nucleic acids, glucocorticoid hormones, and low-molecular weight substances (n-butyrate, 5-bromodeoxy uridine). At least 23 different variants of IFN-α are known. The individual proteins have molecular masses between 19-26 kDa and consist of proteins with lengths of 156-166 and 172 amino acids.

All IFN-α subtypes possess a common conserved sequence region between amino acid positions 115-151 while the amino-terminal ends are variable. Many IFN-α subtypes differ in their sequences at only one or two positions. Naturally occurring variants also include proteins truncated by 10 amino acids at the carboxy-terminal end. Disulfide bonds are formed between cysteines at positions 1/98 and 29/138. The disulfide bond 29/138 is essential for biological activity while the 1/98 bond can be reduced without affecting biological activity.

There are at least 23 different IFN-α genes. They have a length of 1-2 kb and are clustered on human chromosome 9p22. IFN-α genes do not contain intron sequences found in many other eukaryotic genes. Based upon the structures two types of IFN-α genes, designated class I and II, are distinguished. They encode proteins of 156-166 and 172 amino acids, respectively.

All known subtypes of IFN-α show the same antiviral antiparasitic, antiproliferative activities in suitable bioassays although they may differ in relative activities. Human IFN-α is also a potent antiviral substance in murine, porcine, and bovine cell systems. A number of assays for IFN-α have been described. For example, IFN-α can be assayed by a cytopathic effect reduction test employing human and bovine cell lines. Minute amounts of IFN-α can be assayed also by detection of the Mx protein specifically induced by this interferon. A sandwich ELISA employing bispecific monoclonal antibodies for rapid detection (10 units/mL=0.1 ng/mL within 2-3 hours) is also available.

Interferon gamma (γ): IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELSA test that allows detection of individual cells producing IFN-γ. Minute amounts of IFN-γ can be detected indirectly by measuring IFN-induced proteins such as Mx protein. The induction of the synthesis of IP-10 has been used also to measure IFN-γ concentrations. In addition, bioassays can be used to detect IFN-γ, such as an assay that employs induction of indoleamine 2,3-dioxygenase activity in 2D9 cells.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K-Type Oligodeoxynucleotide (K ODN): An oligodeoxynucleotide including an unmethylated CpG motif that has a sequence represented by the formula:

5' $N_1N_2N_3Q\text{-}CpG\text{-}WN_4N_5N_6$ 3'    (SEQ ID NO: 22)

wherein the central CpG motif is unmethylated, Q is T, G or A, W is A or T, and $N_1$, $N_2$, $N_3$, $N_4$, $N_5$, and $N_6$ are any nucleotides. In one embodiment, Q is a T. An additional detailed description of K ODN sequences and their activities can be found below. Generally K ODNs can stimulate a humoral response. For example, K ODNs stimulate the production of immunoglobulins, such as IgM and IgG. K ODNs can also stimulate proliferation of peripheral blood mononuclear cells and increase expression of IL-6 and/or IL-12, amongst other activities.

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Nucleic acid: A deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence and stimulates (e.g. has a mitogenic effect or induces cytokine production) vertebrate immune cells. The cytosine, guanine is unmethylated.

An "oligonucleotide delivery complex" is an oligonucleotide associated with (for example, ionically or covalently bound to; or encapsulated within) a targeting means (such as a molecule that results in a higher affinity binding to a target cell (B cell or natural killer (NK) cell) surface and/or increased cellular uptake by target cells). Examples of oligonucleotide delivery complexes include oligonucleotides associated with: a sterol (for example, cholesterol), a lipid (for example, cationic lipid, virosome or liposome), or a target cell specific binding agent (for example, a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional (Gursel, *J. Immunol.* 167:3324, 2001).

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in the methods and compositions disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Salts encompassed within the term "pharmaceutically acceptable salts" refer to non-toxic salts. In one example, preparation of a salt, such as of an agonists of ADAM-10, are prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate.

Preventing or treating a disease: "Preventing" a disease refers to inhibiting the full development of a disease, for example in a person who is known to have a predisposition to a disease, such as tumor or a disease caused by a pathogen, such as a virus or a bacteria. An example of a person with a known predisposition is someone with a history of diabetes in the family, or who has been exposed to factors that predispose the subject to a condition. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Self-complementary nucleic acid sequence: A nucleic acid sequence that can form Watson-Crick base pairs. The four bases characteristic of deoxyribonucleic unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that could form hydrogen bonds with 3, 4, 5, 6 or more bases, respectively, of the same nucleic acid sequence.

Therapeutically effective dose: A dose sufficient to prevent advancement, or to cause regression of the disease, or which is capable of relieving symptoms caused by the disease, such as pain or swelling.

Vaccine: A preparation of attenuated microorganisms (including but not limited to bacteria and viruses), living microorganisms, antigen, or killed microorganisms, administered for the prevention, amelioration or treatment of infectious disease.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned in this Detailed Description are incorporated by reference in their entirety. In case of conflict, the present specification, including explanations of terms, will control. In addition, the materials, methods, and examples are illustrative only and not intended to be limiting.

II. Specific Embodiments

It is disclosed herein that agents that affect the activity and/or expression of CXCL16 can be used in conjunction with a D-type oligodeoxynucleotide (ODN). Specific compositions including one or more D-type ODNs and an agent that modulates that activity and/or expression of CXCL16 are provided herein. These compositions are of use to induce an immune response. The immune response can be to any antigen of interest, including by not limited to, an antigen from a pathogen or a tumor.

A. D Oligodeoxynucletotides (ODNs)

D ODNs (also known as "A" class ODNs) differ both in structure and activity from K ODNs (also known as "B" class ODNs) and a third type of ODNs, known as "C" class ODNs. For example, as disclosed herein, D ODNs stimulate the release of cytokines from cells of the immune system, and induce the maturation of dendritic cells. In specific, non-limiting examples D ODNs stimulate the release or production of IP-10 and IFN-α by monocytes and/or plasmacytoid dendritic cells.

With regard to structure, in one embodiment, a CpG motif in a D ODN has been described by the formula:

wherein the central CpG motif is unmethylated, R is A or G (a purine), and Y is C or T (a pyrimidine). D-type oligonucleotides include an unmethylated CpG dinucleotide. Inversion, replacement or methylation of the CpG reduces or abrogates the activity of the D oligonucleotide.

In one embodiment, a D-type ODN is at least about 16 nucleotides in length and includes a sequence represented by the formula:

wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1\ Py_2\ CpG\ Pu_3\ Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN, these nucleotides are termed the 5' far-flanking region. Nucleotides 3' of $X_4X_5X_6$ in the D ODN are termed the 3' far-flanking region.

In one specific, non-limiting example, $Py_2$ is a cytosine. In another specific, non-limiting example, $Pu_3$ is a guanidine. In yet another specific, non limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific, not limiting example, N is from about 4 to about 8. In another specific, non-limiting example, N is about 6.

In several embodiments, the D ODN is at least about 16 nucleotides in length. For example, the D ODNs can be from about 16 to about 50 nucleotides in length, or from about 18 to about 50 nucleotides in length, or from about 18 to about 40 nucleotides in length, or from about 18 to about 30 nucleotides in length. Exemplary D ODNs are disclosed below.

D ODNs can include modified nucleotides. Without being bound by theory, modified nucleotides can be included to increase the stability of a D ODN. Without being bound by theory, because phosphothioate-modified nucleotides confer resistance to exonuclease digestion, the D ODNs are "stabilized" by incorporating phosphothioate-modified nucleotides. In one embodiment, the CpG dinucleotide motif and its immediate flanking regions include phosphodiester rather than phosphothioate nucleotides. In one specific, non-limiting example, the sequence $Pu_1\ Py_2\ CpG\ Pu_3\ Py_4$ includes phosphodiester bases. In another specific, non-limiting example, all of the bases in the sequence $Pu_1\ Py_2\ CpG\ Pu_3\ Py_4$ are phosphodiester bases. In yet another specific, non-limiting example, $X_1X_2X_3$ and $X_4X_5X_6(W)_M(G)_N$ include phosphodiester bases. In yet another specific, non-limiting example, $X_1X_2X_3\ Pu_1\ Py_2\ CpG\ Pu_3\ Py_4\ X_4X_5X_6(W)_M(G)_N$ (SEQ ID NO:21) include phosphodiester bases. In further non-limiting examples the sequence $X_1X_2X_3$ includes at most one or at most two phosphothioate bases and/or the sequence $X_4X_5X_6$ includes at most one or at most two phosphothioate bases. In additional non-limiting examples, $X_4X_5X_6(W)_M(G)_N$ includes at least 1, at least 2, at least 3, at least 4, or at least 5 phosphothioate bases. Thus, a D ODN can be a phosphothioate/phosphodiester chimera.

As disclosed herein, any suitable modification can be used to render the D ODN resistant to degradation in vivo (for example, via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D-type oligodeoxynucleotides can also be modified to contain a secondary structure (e.g., stem-loop structure). Without being bound by theory, it is believed that incorporation of a stem-loop structure renders an oligodeoxynucleotide more effective.

In a further embodiment, $Pu_1\ Py_2$ and $Pu_3\ Py_4$ are self-complementary. In another embodiment, $X_1X_2X_3$ and $X_4X_5X_6$ are self-complementary. In yet another embodiment $X_1X_2X_3\ Pu_1\ Py_2$ and $Pu_3\ Py_4\ X_4X_5X_6$ are self-complementary.

Specific non-limiting examples of a D ODN wherein $Pu_1\ Py_2$ and $Pu_3\ Py_4$ are self-complementary include, but are not limited to, AT<u>CG</u>AT, AC<u>CG</u>GT, AT<u>CG</u>AC, AC<u>CG</u>AT, GT<u>CG</u>AC, or GC<u>CG</u>GC (wherein the CpG is underlined). Without being bound by theory, the self-complementary base sequences can help to form a stem-loop structure with the CpG dinucleotide at the apex to facilitate immunostimulatory functions. Thus, in one specific, non-limiting example, D ODNs wherein $Pu_1\ Py_2$ and $Pu_3\ Py_4$ are self-complementary induce higher levels of IFN-γ production from a cell of the immune system. The self-complementary need not be limited to $Pu_1\ Py_2$ and $Pu_3\ Py_4$. Thus, in another embodiment, additional bases on each side of the three bases on each side of the CpG-containing hexamer form a self-complementary sequence (see above).

One specific, non-limiting example of a sequence wherein $Pu_1\ Py_2$ and $Pu_3\ Py_4$ are self-complementary but wherein the far-flanking sequences are not self-complementary is (DV113, SEQ ID NO: 6, see Table 1)
GGTGCATCGATACAGGGGGG This oligodeoxynucleotide has a far-flanking region that is not self-complementary and induces high levels of IFN-γ and IFN-α.

Another specific, non-limiting example of a D ODN is:

(DV28, SEQ ID NO: 3, see Table 1)
GGTGCGTCGATGCAGGGGGG

This D ODN is of use for inducing production and/or release of cytokines from immune cells, although it lacks a self-complementary motif.

In one embodiment, the D ODNs are at least about 16 nucleotides in length. In a second embodiment, a D ODN is at least about 18 nucleotides in length. In another embodiment, a D ODN is from about 16 nucleotides in length to about 100 nucleotides in length. In yet another embodiment, a D ODN is from about 16 nucleotides in length to about 50 nucleotides in length. In a further embodiment, a D ODN is from about 18 nucleotides in length to about 30 nucleotides in length.

In another embodiment, the D ODN is at least 18 nucleotides in length, and at least two G's are included at the 5' end of the molecule, such that the oligodeoxynucleotide includes a sequence represented by the formula:

$$5'\ GGX_1X_2X_3\ Pu_1\ Py_2\ CpG\ Pu_3\ Py_4\ X_4X_5X_6(W)_M\ (G)_N\text{-}3'.$$

The D ODN can include additional G's at the 5' end of the oligodeoxynucleotide. In one specific example, about 1 or about 2 G's are included at the 5' end of an oligodeoxynucleotide including a sequence as set forth as the above formula.

Examples of a D ODN include, but are not limited to the sequence shown in the following table:

TABLE 1*

| ODN D ODN | SEQUENCE | SEQUENCE IDENTIFIER |
|---|---|---|
| DV104 | GGTGCATCGATGCAGGGGGG | (SEQ ID NO: 1) |
| DV19 | GGTGCATCGATGCAGGGGGG | (SEQ ID NO: 1) |
| DV29 | GGTGCACCGGTGCAGGGGGG | (SEQ ID NO: 2) |
| DV35 | GGTGCATCGATGCAGGGGGG | (SEQ ID NO: 1) |
| DV28 | GGTGCGTCGATGCAGGGGGG | (SEQ ID NO: 3) |
| DV106 | GGTGTGTCGATGCAGGGGGG | (SEQ ID NO: 4) |
| DV116 | TGCATCGATGCAGGGGGG | (SEQ ID NO: 5) |
| DV113 | GGTGCATCGATACAGGGGGG | (SEQ ID NO: 6) |
| DV34 | GGTGCATCGATGCAGGGGGG | (SEQ ID NO: 7) |
| DV102 | GGTGCATCGTTGCAGGGGGG | (SEQ ID NO: 8) |
| DV32 | GGTGCGTCGACGCAGGGGGG | (SEQ ID NO: 9) |

TABLE 1*-continued

| ODN D ODN | SEQUENCE | SEQUENCE IDENTIFIER |
|---|---|---|
| DV117 | GGTCGATCGATGCACGGGGG | (SEQ ID NO: 10) |
| DV37 | GGTGCATCGATGCAGGGGGG | (SEQ ID NO: 11) |
| DV25 | GGTGCATCGATGCAGGGGGG | (SEQ ID NO: 11) |
| DV30 | GGTGCATCGACGCAGGGGGG | (SEQ ID NO: 12) |
| dv120 | GGTGCATCGATAGGCGGGGG | (SEQ ID NO: 13) |
| DV27 | GGTGCACCGATGCAGGGGGG | (SEQ ID NO: 14) |
| dv119 | CCTGCATCGATGCAGGGGGG | (SEQ ID NO: 15) |
| D142 | GGTATATCGATATAGGGGGG | (SEQ ID NO: 16) |
| d143 | GGTGGATCGATGCAGGGGGG | (SEQ ID NO: 17) |

Underlined bases are phosphodiester.
*indicates methylated CG.
Bold indicates self-complementary sequences.
Sequence identifier is noted below the nucleic acid sequence.

Additional exemplary D ODN sequences can be found in U.S. patent application Ser. No. 10/068,160, and in Verthelyi et al., *J. Immunol.* 166:2372-2377, 2001, which are both herein incorporated by reference in their entireties. D ODN can be used in combination to induce an immune response. Thus, multiple D ODNs can be utilized to induce an immune response. For example, two, three, four, five or more D ODNs can be utilized to induce an immune response. In addition, a single ODN can be generated that includes the two or more D ODN CpG motifs disclosed herein.

The D ODN can be synthesized de novo using any of a number of procedures well known in the art. For example, the oligodeoxynucleotides can be synthesized as set forth in U.S. Pat. No. 6,194,388, which is herein incorporated by reference in its entirety. A D ODN can be synthesized using, for example, the B-cyanoethyl phosphoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

The response elicited by D, K and C ODNs is dependent on Tol-like receptor 9 (TLR9). Cells lacking TLR9 are unresponsive to any form of CpG ODNs. It is disclosed herein that an additional receptor is required for optimal recognition of D ODN, namely CXCL16. Altering the expression of activity of this receptor can be used to alter an immune response induced by a D ODN.

Methods of Altering an Immune Response

A method is disclosed herein for altering the uptake of a D ODN. Increasing the uptake of a D ODN can be used to increase the immunostimulatory activity of the D ODN. Similarly, decreasing the uptake of a D ODN can be used to attenuate the immunostimulatory activity of the D ODN.

As described above, D ODNs are of use in producing an immune response (see also PCT Publication Nos. WO0061151A3, WO9956755A1, WO9840100A1, WO9818810A1, WO0122990A2, which are all herein incorporated by reference in their entirety). Administration of a D ODN can be by any suitable method, including in vivo or ex vivo administration. For example, a D ODN can be used to stimulate monocytes and/or natural killer cells, and/or to induce the maturation of dendritic cells. Furthermore, a D ODN can be used to increase the production of cytokines (for example IP-10, IFN-α or IFN-γ) by a cell of the immune system. D ODNs can be used to induce a T cell response to an antigen of interest. D ODNs are also of use in producing an immune response against pathogens (such as bacterial, viral, or fungal pathogens). D ODNs can be used to induce a protective immune response. D ODNs can be used to increase an immune response to a tumor antigen. Thus, D ODNs are of use in a variety of therapeutic applications, and can also be utilized in vaccine formulations.

An agent that increases the activity and/or expression of CXCL16 can be used to increase one or more immune response induced by a D ODN. In one embodiment, a method is provided for increasing the uptake of a D ODN. The method includes administering an effective amount of an agent that increases the activity and/or expression of CXCL16. In another embodiment, a method is disclosed herein for inducing an immune response in a subject by administering a D ODN and an agent that increases the activity and/or expression of CXCL16. The immune response can include, but is not limited to, induction of the maturation of a dendritic cell or the activation of a natural killer cell and/or a monocyte. The immune response can also include the production of a cytokine, such as, for example, IL-10, IP-10, IFN-α or IFN-γ. The immune response can also include an immune response against an antigen, such as a bacterial, viral, or fungal antigen.

The immune response can include an immune response to a tumor antigen. In one example, a D ODN is administered in conjunction with an agent that increases the expression and/or activity of CXCL16 to a subject that has an autoimmune disease. Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like. Specific, non-limiting examples of autoimmune diseases include, but are not limited to diabetes, rheumatoid arthritis, lupus erythematosus, and multiple sclerosis.

In another example, a D ODN is administered in conjunction with an agent that increases the expression and/or activity of CXCL16 to treat, prevent, or ameliorate an allergic reaction in a subject. An allergy refers to an acquired hypersensitivity to a substance (an allergen). Allergic conditions include eczema, allergic rhinitis or coryza, hay fever, bronchial asthma, uticaria (hives), food allergies, and other atopic conditions. The list of allergens is extensive and includes pollens, insect venoms, animal dander, dust, fungal spores, and drugs (such as antibiotics like penicillin or tetracycline). Examples of natural, animal, and plant allergens can be found in PCT Publication No. WO 98/18810. In one embodiment a D ODN is administered to a subject in conjunction with an agent that increases the expression and/or activity of CXCL16 to treat an allergic condition such as allergic asthma. The D ODN and the agent that increases the uptake and/or activity of CXCL16 can also be administered in combination with an anti-allergenic agent. Suitable anti-allergenic agents include those substances given in treatment of the various allergic conditions described above, examples of which can be found in the Physicians' Desk Reference (1998).

In a further example, a D ODN is administered to a subject that has a neoplasm. In one embodiment, the subject has cancer. The D ODN is administered in conjunction with an agent that increases the expression and/or activity of CXCL16. The D ODN and the agent that increases the expression and/or activity of CXCL16 can be administered either alone or in combination with any suitable anti-neoplastic agent, such as a chemotherapeutic agent or radiation. Suitable neoplasms include benign and malignant cancer. The neoplasm can be from any origin, and include, but are not limited to, solid tumors such as cancers of the brain, lung (e.g., small cell and non-small cell), ovary, breast, prostate, liver, lung, skin, and colon, as well as carcinomas and sarcomas. The neoplasm can also be a lymphoma or a leukemia. Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). The administration of the D ODN and the agent that increases the expression and/or activity of CXCL16 can be used to reduce tumor burden.

In yet another example, a method is provided to enhance the efficacy of any suitable vaccine. The method includes the administration of a D ODN in conjunction with an agent that increases the expression and/or activity of CXCL16 and a vaccine component. Suitable vaccines include those directed against Leishmania, Hepatitis A, B, and C, examples of which can be found in the Physicians' Desk Reference (1998), and DNA vaccines directed against, for example, malaria. (See generally Klinman et al., *Vaccine* 17:19, 1999; McCluskie and Davis, *J. Immun.* 161:4463, 1998). The vaccine can be a subunit vaccine, or can include an attenuated or heat-killed virus.

In an additional example, D ODN and the agent that induces the expression and/or activity CXCL16 can be used to treat or ameliorate any condition associated with an infectious agent. Thus, the D ODN and the agent that increases the activity and/or expression of CXCL16 can be administered to a subject infected with the infectious agent. Specific, non-limiting examples of conditions associated with infectious agents are tularemia, francisella, schistosomiasis, tuberculosis, malaria, and leishmaniasis. Examples of infectious agents are viruses, bacteria, fungi, and other organisms (such as protists) can be found in PCT Publication No. WO 98/18810. The D ODN and the agent that induces the expression and/or activity of CXCL16 can be administered in combination with any suitable anti-infectious agent, such as an antiviral, anti-fungal or anti-bacterial agent (see Physicians' Desk Reference, 1998).

The agent that increases the activity and/or expression of CXCL16 can be one or more cytokines. The cytokines interferon gamma (IFN-γ, see, for example GENBANK® Accession No. AAM28885, May 16, 2002) and tumor necrosis factor alpha (TNF-α, see, for example GENBANK® Accession No. NP_000585, Aug. 20, 2006, incorporated herein by reference) induce CXCL16, either alone or in combination. Thus, IFN-γ and/or TNF-α could be used to increase the uptake of a D ODN. Nucleic acids encoding IFN-γ or TNF-α could be administered to the subject in order increase the uptake of a D ODN. The agents that induce the expression and/or activity of CXCL16 include nucleic acids encoding CXCL16, such as human CXCL16.

Agents that increase the activity and/or expression of CXCL16 include, but are not limited to, antagonists of ADAM-10. Exemplary antagonists of ADAM-10 are GW280264X, GI254023X or GM6001. GM6001 has the chemical formula $C_{20}H_{28}N_4O_4$, and has the structure shown below:

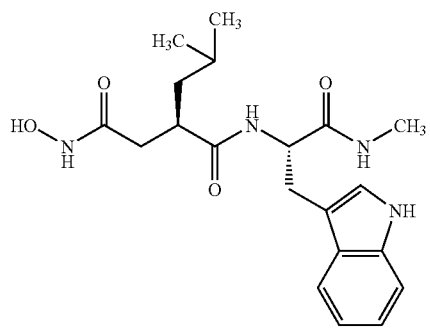

GW280264X ((2R,3 S)-3-(formyl-hydroxyamino)-2-(2-methyl-1-propyl) hexanoic acid [(1S)-5-benzyloxycarbamoylamino-1-(1,3-thiazol-2-ylcarbamoyl)-1-pentyl]amide) and GI254023X((2R,3S)-3-(formyl-hydroxyamino)-2-(3-phenyl-1-propyl) butanoic acid[(1S)-2,2-dimethyl-1-methylcarbamoyl-1-propyl]amide) can be synthesized as described in U.S. Pat. No. 6,172,064, U.S. Pat. No. 6,191,150 and U.S. Pat. No. 6,329,400. The compounds can be administered as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof. These compounds can also be administered as pharmaceutically acceptable salt, solvate, biohydrolyzable ester, biohydrolyzable amide, affinity reagent, or prodrug thereof for use in therapy.

Other MMP-2 inhibitors are of use, such as batimastat. In addition, an inhibitor such as inhibitor of the formula $C_{18}H_{35}NO_2$:

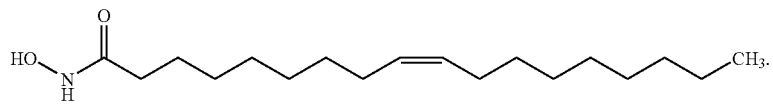

Also of use is an inhibitor of the formula $C_{13}H_{14}N_4O_3S_2$:

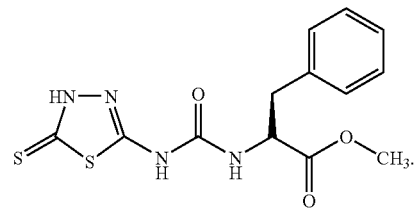

Also of use is an inhibitor of the formula $C_{21}H_{23}N_7O_2S_2$:

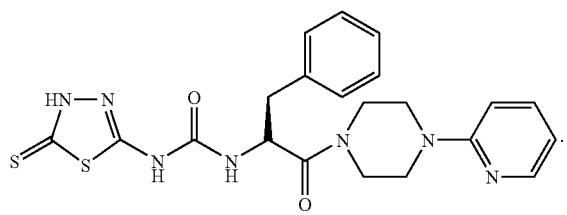

Also of use is an inhibitor of the formula $C_{21}H_{19}NO_4S$:

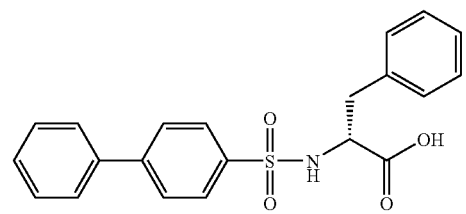

Additional agents can be administered in conjunction with the D ODN and the agent that alters the activity and/or expression of CXCL16. These agents include a protein, an antigenic epitope, a hydrocarbon, lipid, mitogen, an anti-infectious agent (such as antiviral, antifungal, or anti-bacterial agent), a chemotherapeutic agent or a vaccine (such as a live, attenuated, or heat-killed vaccine). Additional agents can be administered simultaneously or sequentially with the D ODN and the agent that increases the activity and/or expression of CXCL16.

In one embodiment, a method is provided for activating an antigen presenting cell or lymphocyte in vitro. The method includes contacting a monocyte or a dendritic cell precursor in vitro with a D ODN and an agent that increases CXCL16 expression and/or activity to produce an activated antigen presenting cell. The monocytes or dendritic cell precursors can be contacted with the D ODN and the agent that increases CXCL16 expression and/or activity in the presence of or in the absence of an antigen. The activated antigen presenting cell can be administered to the subject to induce an immune response. Alternatively, lymphocytes or natural killer cells are contacted with the activated antigen presenting cells in vitro, or with cytokines secreted by the activated antigen presenting cells in vitro, to produce activated lymphocytes or activated natural killer cells. The activated lymphocytes or natural killer cells can then be administered to the subject to induce an immune response.

In another embodiment, a method is provided for decreasing the uptake of a D ODN. The method includes providing an agent that decreases the activity and/or expression of CXCL16. In one example, the agent that decreases the uptake of a D ODN is ionomycin. In another example, the agent that decreases the activity and/or expression of CXCL16 is an antisense oligonucleotide, small inhibitory mRNA (simRNA) or a ribozyme that cleaves CXCL16 mRNA. One of skill in the art can readily produce these molecules using the CXCL nucleic acid sequence and/or protein sequence.

In a further example, the agent that decreases the activity and/or expression of CXCL16 is an antibody. The antibody or antibody fragment can be a humanized immunoglobulin. Generally, the humanized immunoglobulin specifically binds to the CXCL16, or a molecule that regulates CXCL16, with an affinity constant of at least $10^7$ M$^{-1}$, such as at least $10^8$ M$^{-1}$ or $10^9$ M$^{-1}$. The use of antibody components derived from humanized monoclonal antibodies obviates potential problems associated with the immunogenicity of the constant regions of the donor antibody. Techniques for producing humanized monoclonal antibodies are described, for example, by Jones, et al., *Nature* 321:522, 1986; Riechmann, et al., *Nature* 332:323, 1988; Verhoeyen, et al., *Science* 239: 1534, 1988; Carter, et al., *Proc. Nat'l Acad. Sci. U.S.A.* 89:4285, 1992; Sandhu, *Crit. Rev. Biotech.* 12:437, 1992; and Singer, et al., *J. Immunol.* 150:2844, 1993.

Antibodies include intact molecules as well as fragments thereof, such as Fab, F(ab')$_2$, and Fv which include a heavy chain and light chain variable region and are capable of binding the epitopic determinant. These antibody fragments retain some ability to selectively bind with their antigen or receptor and are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics Agents that increase intracellular calcium are of use in decreasing CXCL16 activity. Without being bound by theory, agents that increase intracellular calcium are of use in increasing ADAM-10 activity resulting in increased cleavage of CXCL-16. For example, a cross-linking agent can be used to cross link the BDCA-2 receptor on the surface of plasmacytoid dendritic cells. This results in increased intracellular calcium flux and a corresponding decrease in CXCL16 activity. Plasmacytoid dendritic cells treated with a cross-linking agent fail to produce interferon alpha in response to a D ODN.

CXCL16 plays a role in atherosclerosis and Alzheimer's disease. Thus, reduced levels of CXCL16 can be used to treat subjects with atherosclerosis and Alzheimer's disease. Reducing CXCL16 on the surface of plasmacytoid dendritic cells can also be effective in treating SLE. Thus, a method is provided herein for the treatment of subjects with atherosclerosis, Alzheimer's disease, and systemic lupus Erythematosus. In several examples, the method includes administering an antibody that specifically binds CXCL16, an agent that increases the activity of ADAM-10, such as ionomycin.

For use in vivo, generally a pharmaceutical composition including a therapeutically effective amount of the agent that alters CXCL16 expression and/or activity is administered to the subject of interest. A D ODN is also administered to the subject of interest. In one example, the agent that alters CXCL16 expression and/or activity can be included in the same composition as the D ODN. Thus, compositions are provided herein that include a therapeutically effective amount agent that alters CXCL16 and a therapeutically effective amount D ODN in a pharmaceutically acceptable carrier. Optionally, additional therapeutic agents can be included, such as, but not limited to chemotherapeutic agents, antigens, attenuated or heat killed virus, and/or cytokines. However, the CXCL16 can be included in a first composition, and the D ODN included in a second composition, and the two compositions administered to a subject of interest sequentially.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. Agents that increase the expression and/or activity of CXCL-16 and D ODN can be administered systemically or locally. The agents can be administered in oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation form, all using forms well known to those of ordinary skill in the art.

For instance, in addition to injectable fluids, topical and oral formulations can be employed. Topical preparations can include eye drops, ointments, sprays and the like. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

For example, oral dosages of antagonists of ADAM-10, when used for the indicated effects, will range between about 0.1 to 2000 mg/kg of body weight per day, and particularly 1 to 1000 mg/kg of body weight per day. Oral dosage units are generally administered in the range of from 1 to about 250 mg, such as from about 25 to 250 mg. The daily dosage for a 70 kg mammal can be, for example, in the range of about 10 mg to 5 grams of a compound. The dosage regimen is generally selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe a therapeutically effective amount.

In some embodiments, pharmaceutical compositions will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. See for example, U.S. Pat. No. 6,172,064, for a discussion of the preparation of tablets capsules, suppositories, formulations for injection, and formulations for inhalation therapy, such as for use with ADAM-10 inhibitors.

Compositions can be formulated with an appropriate solid or liquid carrier, depending upon the particular mode of administration chosen. If desired, the disclosed pharmaceutical compositions can also contain minor amounts of non-toxic auxiliary substances, such as wetting or emulsifying agents, preservatives, and pH buffering agents and the like, for example sodium acetate or sorbitan monolaurate. Excipients that can be included in the disclosed compositions include flow conditioners and lubricants, for example silicic acid, talc, stearic acid or salts thereof, such as magnesium or calcium stearate, and/or polyethylene glycol, or derivatives thereof.

The compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Therapeutic compositions can be formulated in unit dosage form, suitable for individual administration of precise dosages. In pulse doses, a bolus administration is provided, followed by a time-period wherein no disclosed agent that affects CXCL16 activity/D ODN is administered to the subject, followed by a second bolus administration. A therapeutically effective amount of the composition can be administered in a single dose, or in multiple doses, for example daily, during a course of treatment. In specific, non-limiting examples, pulse doses are administered during the course of a day, during the course of a week, or during the course of a month.

A form of repository or "depot" slow release preparation can be used so that therapeutically effective amounts of the preparation are delivered into the bloodstream over many hours or days following transdermal injection or delivery. Such long acting formulations can be administered by implantation (for example subcutaneously or intramuscularly) or by intramuscular injection. The compounds can be formulated with suitable polymeric or hydrophobic materials (for example as an emulsion in an acceptable oil) or ion exchange resins, or as sparingly soluble derivatives, for example, as a sparingly soluble salt.

The therapeutic compositions that can be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, compositions including an agent that affects CXCL16 activity and/or expression are administered by sustained-release systems. The D ODN can also be administered by sustained release systems, alone or in combination with the agent that affects CXCL16 activity and/or expression. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

Screening for Agents that Alter an Immune Response

An in vitro method is provided herein for screening for an agent that affects the immune response induced by a D ODN. In one example, the method includes contacting a cell with an agent in vitro, and assessing the expression and/or activity of CXCL16. An increase in the expression and/or activity of CXCL16 indicates that the agent is of use in increasing the uptake of a D ODN. An increase in the expression or activity of CXCL16 also indicates that the agent will increase an immune response induced by an ODN. A decrease in the expression and/or activity of CXCL16 indicates that the agent is of use in decreasing the uptake of a D ODN. A decrease in the expression or activity of CXCL16 also indicates that the agent will decrease an immune response induced by an ODN.

A parameter of an immune response can also be measured. In one embodiment, cytokine production is measured. For example, the production of interferon-α or IL-6 can be measured. In another embodiment, expression of a protein is assess, such as, but not limited to, the expression of HLA.

The expression or activity of CXCL16 can be measured by any method known to those of skill in the art. For example, the expression of CXCL16 can be measured by polymerase chain reaction, Western blot, and ELISA and flow cytometry (see Abel et al., *J. Immunol.* 172:6362-6372, 2004, incorporated herein by reference for a detailed description of these methods).

One exemplary non-limiting method for measuring CXCL16 is reverse transcriptase polymerase chain reaction (RT-PCR). One exemplary non-liming method utilizes RNA isolated from cultured cells using TRIzol reagent. Total RNA (1 µg) is treated with DNaseI and is reverse transcribed to cDNA using a suitable commercially available polymerase. For each sample, a control without polymerase is run parallel to allow assessment of genomic DNA contamination. Each cDNA sample is analyzed for expression of CXCL16 and GAPDH by real-time quantitative RT-PCR using the fluorescent TAQMAN™ 5'-nuclease assay. Exemplary sequences of forward primer, reverse primer, and probe for CXCL16 are 5'-GAG CTC ACT CGT CCC AAT GAA-3' (SEQ ID NO: 18), 5'-TCA GGC CCA ACT GCC AGA C-3' (SEQ ID NO: 19), and 5'-FAM CAC CAT TCA CAC TGC GGG CCA C TAMRA-3' (SEQ ID NO: 20). Levels of CXCL16 mRNA can be quantified by comparison of the fluorescence of each sample with that of a serially diluted standard of human genomic DNA.

One exemplary and non-limiting method for an ELISA assay for a CXCL16 is as follows: Microlon 96-well plates (Greiner, Nurtingen, Germany) at room temperature, are utilized with a reaction volume was 50 µl. The plate is coated overnight with 2 mg/ml goat anti-human CXCL16 in 50 mM $Na_2CO_3$ (pH9.3), washed three times with 0.05% TWEEN in phosphate buffered saline (PBS-T), and blocked with PBS-T containing 2% bovine serum album (BSA) for 2 hours. The plate is dried and the samples are added for 2 hours. A standard prepared as nine serial ½ dilutions of 1.25 nM recombinant human CXCL16 in either PBS-T with 1% BSA, serum-free medium, or cell lysis buffer is run in parallel. Following washing, 200 ng/ml biotinylated rabbit anti-human CXCL16 in PBS-T/1% BSA is added to each well and the plate is incubated at room temperature for 1 hour. After washing, 100 mU/ml streptavidin-peroxidase conjugate (Roche) in PBS-T/1% BSA is added for 1 hour. After washing, chromogenic peroxidase substrate is added. The reaction is stopped after a twenty-minute incubation by addition of 1.8 M $H_2SO_4$ before the optical density (OD) was determined at 450 nm.

One exemplary and non-limiting method for FACS analysis of CXCL16 expression is as follows: cells are suspended in ice-cold PBS containing 0.1% BSA and 0.01% $NaN_3$ at $3 \times 10^5$ cells/ml and incubated with purified rabbit anti-human CXCL16 or rabbit IgG control (both at 2 µg/ml in PBS with 0.1% BSA and 0.01% $NaN_3$) for 1 hour on ice. Following two-fold washing, cells are incubated with secondary fluorescein-conjugated goat anti-rabbit IgG for 1 hour on ice. Cells are washed twice and suspended in ice-cold PBS containing 2% paraformaldehyde. The fluorescence signal of the labeled cells is then analyzed by flow cytometry, and calculated as median fluorescence intensity (MFI) of the cell population.

The expression or activity of CXCL16 can be compared to a control. Suitable controls also include a standard value or a cell contacted with the D ODN in the absence of the agent.

An in vivo method is provided herein for screening for an agent that affects the immune response induced by a D ODN. In one example, the method includes administering of the agent to a non-human mammal, such as a mouse, rat, cat, sheep, dog, goat, pig or monkey, and assessing the expression and/or activity of CXCL16 in a sample taken from the non-human mammal.

An increase in the expression and/or activity of CXCL16 indicates that the agent is of use in increasing the uptake of a D ODN. An increase in the expression or activity of CXCL16 also indicates that the agent will increase an immune response induced by an ODN. A decrease in the expression and/or activity of CXCL16 indicates that the agent is of use in decreasing the uptake of a D ODN. A decrease in the expression or activity of CXCL16 also indicates that the agent will decrease an immune response induced by an ODN.

As noted above, the expression or activity of CXCL16 can be measured by any method known to those of skill in the art. For example, the expression of CXCL16 can be measured by polymerase chain reaction, Western blot, and ELISA and flow cytometry (see Abel et al., *J. Immunol.* 172:6362-6372, 2004, for a detailed description of these methods). In addition, an immune response can be evaluated in the animal model. For example, the production of a cytokine or the number of cells (such as activated T cells) can be measured.

The expression or activity of CXCL16 can be compared to a control. Suitable controls also include a standard value. Suitable controls also include a sample obtained from an animal administered the D ODN in the absence of the agent.

The disclosure is illustrated by the following non-limiting Examples.

EXAMPLES

Example 1

Dextran Sulfate Blocks D ODN Uptake and Signaling

To evaluate whether a scavenger receptor (SR) played a role in D ODN uptake and signaling, the ability of dextran sulfate and fucoidan (classical scavenger receptor ligands) to block the binding of CpG ODN to pDC was evaluated (Table 2 and Supplementary FIG. 3A).

TABLE 2

Effect of dextran sulfate on cellular activation induced by CpG ODN

| Effect of Dextran Sulfate | K ODN | D ODN |
|---|---|---|
| % inhibition of binding to pDC[a] | 23.2 ± 8.8 | 65.02 ± 5.8 |
| % inhibition of cytokine secretion[b] | 5.8 ± 2.3 | 90.3 ± 8.4 |
| % inhibition in the generation of HLA-DR/CD54 double positive cells[c] | 0.8 ± 1.8 | 92.3 ± 5.8 |

[a]Purified pDC were preincubated (20 min at 4° C.) with medium or with 50 µg/ml of dextran sulfate followed by addition of 1 µM FITC conjugated ODN. Mean fluorescence intensity representing binding of FITC-ODN was assessed by flow cytometry.
[b]"K" ODN induced TNF-α production and "D" ODN induced IFN-α production from PBMC was determined by intracytoplasmic staining and by ELISA, respectively in the absence or presence of 50 µg/ml of dextran sulfate.
[c]Purified pDC were incubated with 1 µM of "K or with 3 µM "D" ODN in the absence or presence of 50 µg/ml dextran sulfate and upregulation of HLA-DR/CD54 was determined 24 hours later using flow cytometry. Results represent the mean ± S.D of three independent experiments.

Dextran sulfate inhibited the binding of D but not K ODN to pDC by >50% (p<0.001). Similar levels of inhibition were achieved in the presence of another SR ligand fucoidan but not with the non-ligand chondroitin sulfate. These SR ligands also abolished D ODN induced IFNα secretion and up-regulation of HLA-DR/CD54 by >90% (p<0.001) (Table 2 and Supplementary FIGS. 3B and 3D) but failed to affect K ODN induced TNFα production and HLA-DR/CD54 up-regulation (Table 2 and FIGS. 3C and 3D). These results suggested a SR-mediated recognition mechanism for D ODN.

Example 2

Identification of the Receptor for D ODN

To identify the nature of the D ODN receptor, a preliminary screening for multiple SRs (type A SR, CD36, CD163, MARCO and SR-PSOX/CXCL16) provided evidence that CXCL16 might be involved in the recognition of D ODN. CXCL16 is an unusual chemokine with SR activity when expressed as a transmembrane molecule at the surface of professional antigen presenting cells (Shimaoka et al., *J Biol Chem.* 275(52):40663-6, 2000). Based on the initial screening results, the ability of biotin conjugated CpG ODN to bind to purified recombinant CXCL16 was assessed in a cell-free ELISA-based assay and was found to be dose-dependent and significantly higher (P<0.001) for D ODN than the binding levels seen with K ODN (FIG. 1A).

Example 3

Specificity of CXCL16 for D ODN Binding

Next, the specificity of CXCL16 as a potential binding receptor for D ODN was determined in HE 93 cells. The percent of HEK293 cells internalizing large amounts of D ODN rose significantly by >5-fold following transfection with a CXCL16 encoding plasmid (p<0.05, FIG. 1B, histogram) as opposed to no change in the case of K ODN. Confocal microscopy revealed that CXCL16 colocalized with D but not with K ODN (FIG. 1B). Of note, the level of CXCL16 surface expression correlated with the magnitude of D ODN uptake (FIG. 1B, compare cells indicated with open versus filled arrow heads).

To evaluate whether CXCL16 could act as a D ODN-specific cell surface receptor in pDC, expression of this receptor in human pDC was analyzed. Results from flow cytometry studies showed that 20-40% of pDC (FIG. 4A) expressed CXCL16 on their surface. By comparison, Uchiyama et al. (Tabata S. et al., *J Leukoc Biol.* 77(5):777-86, 2005) described that pDC produce CXCL16, but report that most of this material is cleaved and secreted.

Figure 4B:
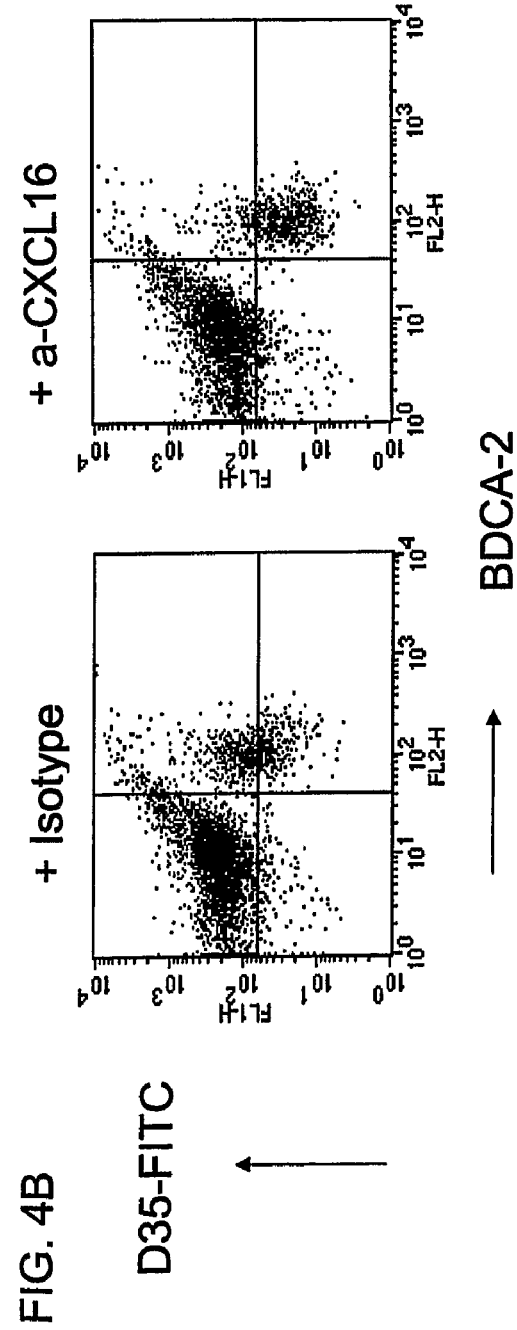

After confirming that pDC express CXCL16 at their surface, ODN binding to this cell type was assessed in the presence of antibodies against CXCL16. Anti-CXCL16 antibodies significantly inhibited the binding of D ODN to pDC (78.39%, P<0.001, FIG. 1C). Isotype-matched control had no effect on any class of CpG ODN binding. Of note, the CXCL16 antibody specifically inhibited D ODN binding only to pDC but not to the BDCA-2 negative CD123+ basophils (FIG. 4B) providing further evidence for the specificity of this inhibition. In contrast, only 10.7% of K ODN binding could be inhibited using anti-CXCL16. These results suggest that CXCL16 is involved in the binding/uptake of D but not K ODN.

Example 4

Expression of CXCL16 and D ODN Stimulation

To assess whether pDCs expressing CXCL16 were more responsive to D ODN stimulation, TNFα and IFNα production from CXCL16[bright] or dim/negative cells was analyzed by intracellular cytokine staining (FIG. 2A). K but not D ODN produced significant amounts of TNFα from pDCs and 83.21±0.74% of all producers were in the CXCL16 negative/dim population. In contrast, D ODNs induced significant amounts of IFNα and almost all of this cytokine (85.51±0.22%) was produced by the CXCL16[positive] pDCs. Furthermore, stimulation of highly pure sorted CXCL16[negative] pDC resulted in up-regulation of HLA-DR/CD86 by K but not by D ODNs, whereas as expected both ODNs showed activity in the sorted CXCL16[positive+negative] population (FIG. 5). Of interest, UV-irradiated HSV-1 showed a very similar activation pattern as observed with D ODNs. These results suggest a preferential stimulation of CXCL16[positive] pDCs by D but not by K ODNs.

Additional studies confirmed that the immunostimulatory activity of D class ODNs required recognition by CXCL16. First, anti-CXCL16 antibodies (Abs) reduced D ODNs dependent IFNα production by 55.9% (p<0.005 when compared to isotype control, FIG. 2B), but had no significant effect on the ability of K ODNs to stimulate IP-10 production. Second, anti-CXCL16 Abs significantly reduced the ability of D (but not K) ODNs to activate pDC as manifest by the up-regulation of HLA-DR/CD86 expression in elutriated monocytes (FIG. 2C, 68.7% suppression as opposed to 1.4% p. <0.001)

Whereas K ODNs strongly induce NF-KB signaling by TLR9 transfected HEK293 cells, D ODNs are much less active (Vollmer et al, *Eur J Immunol.* 34(1):251-62, 2004). As seen in FIG. 6, K ODNs increase NF-kB signaling by nearly 4-fold, versus only 1-1.3-fold by two different D ODNs. Yet when HEK293 cells that stably express TLR9 were transiently transfected with CXCL16, they became highly responsive to D ODN stimulation. The response of CXCL16 transfected TLR9 expressing cells as compared to mock transfected TLR9 expressing cells is presented in FIG. 2D. CXCL16 transfection increases background luciferase activity almost 2-fold for all ODNs irrespective of whether they contain CpG or not except for D class, where significantly higher responses were achieved (6-fold, P<0.05, FIG. 2D) in the presence of CXCL16.

Example 5

ADAM-10

Figure 7A:
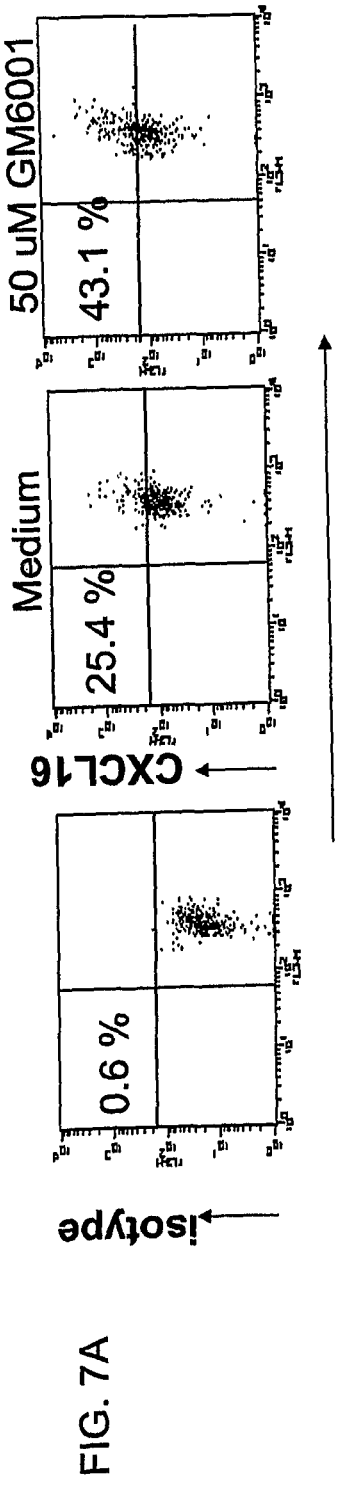
FIGS. 7A-7B are a plot and a bar graph showing the metalloproteinase inhibitor GM-6001 enhances CXCL16 expression and subsequent cytokine production induced by D ODN. PBMC were preincubated in the absence (open bars) or presence (filled bars) of GM-6001 (50 µM) for 30 minutes, washed and then stained for CXCL16 expression on pDC (see FIG. 7A) or stimulated with 1 µM of K or 3 µM D ODN for 24 hours (FIG. 7B). Cytokine production (IL-6 for K ODN and IFN-α D ODN) was assessed from culture supernatants using ELISA. Individual results from six different PBMC are shown.
Figure 7B:
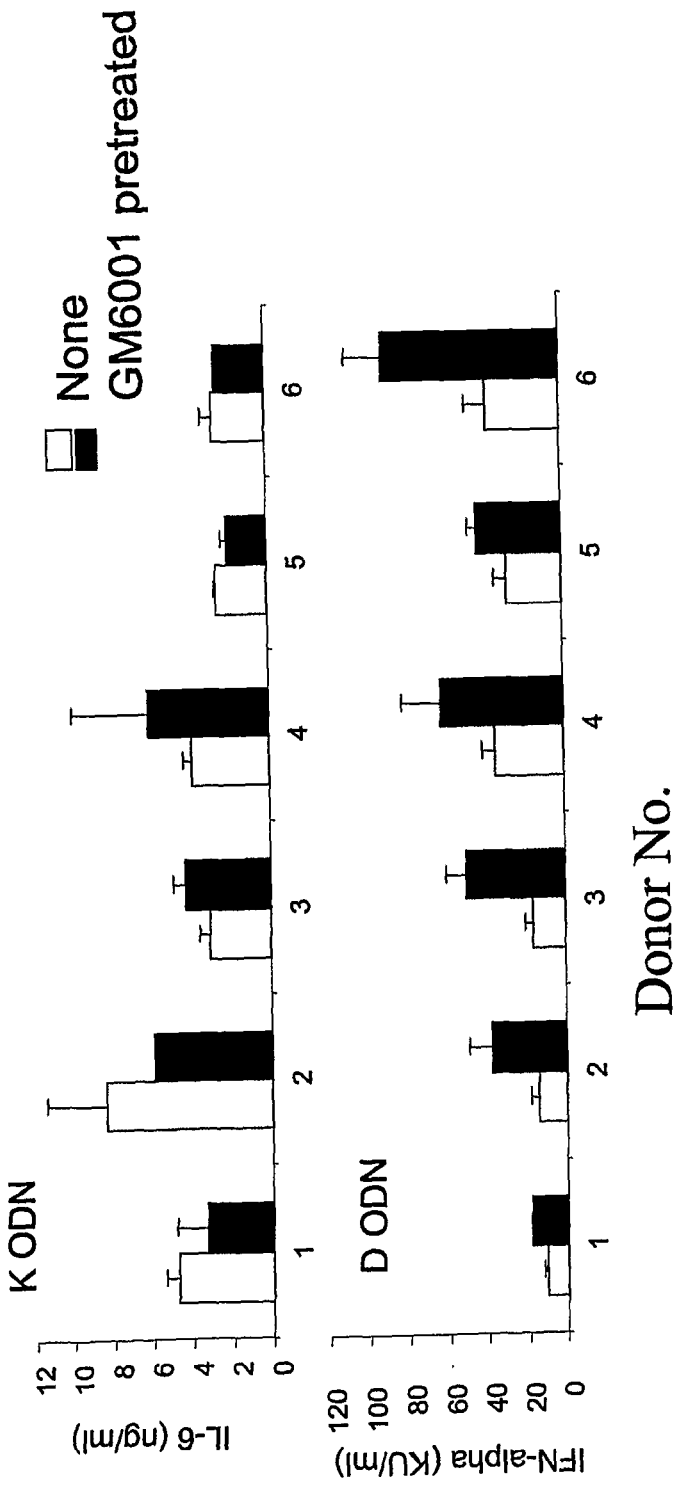

CXCL16 expressed on the cell surface is cleaved by the metalloproteinase ADAM-10 (Abel et al., *J Immunol.* 2004 172(10):6362-72, 2004; Gough et al., *J Immunol.* 172(6): 3678-85, 2004). Previous studies demonstrated that the amount of the cell surface expressed CXCL16 can be increased by treatment with the metalloproteinase inhibitor GM6001. Based on the observation that pDC expressing high levels of CXCL16 were more responsive to D ODN stimulation, human PBMC were incubated with GM6001 followed by K or D ODNs. Metalloproteinase inhibitor treatment increased the expression of CXCL16 (FIG. 7) and D ODN responsiveness (2-fold, p<0.05) of pDCs, but had no effect on cells stimulated with K ODN.

Thus, the scavenger receptor CXCL16 plays a key role in mediating the binding, uptake and subsequent stimulation mediated by D but not K ODNs. Without being bound by theory, the role of CXCL16 in D ODN uptake and activity explains previously observed differences in the targeting and internalization of D ODNs compared to other CpG ODN classes.

As described herein, pDC expressing high levels of that SR were also the most responsive to D ODN activation. Indeed, a significant positive correlation was noted between CXCL16 expression and cytokine (IFNα) production by D ODN stimulated pDC. Consistent with this observation, treatment with a metalloproteinase inhibitor that increased cell surface expression of CXCL16 also increased responsiveness to D ODNs. Finally, it was demonstrated that HEK293 cells transfected with a plasmid encoding CXCL16 significantly increased their capacity to bind D (but not K) ODNs.

HEK293 cells transfected to express TLR9 (the cognate receptor for CpG motifs) responded to stimulation by K ODNs. This observation suggests that K-type CpG ODNs do not require CXCL16 for uptake or activity. In contrast, HE 93 cells transfected with TLR9 alone did not respond to D ODNs, but became responsive when co-transfected with CXCL16. Confocal microscopy of these transfected cells showed that D ODNs colocalized extensively with CXCL16, unlike K ODNs.

The selective binding of D but not K ODNs to CXCL16 could be mediated by the poly G tail unique to D ODNs. The poly G tail present on all D ODNs allows the formation of G-tetrads, and the resultant generation of higher order tertiary structures (Kerkman et al, *J Biol Chem.* 280(9):8086-93, 2005). In this context, it appears that D ODNs, with its nano-particle forming ability, is recognized specifically by the scavenger receptor CXCL16 and this highly specific interaction and subsequent internalization may alter the subcellular distribution of this ODN.

Human pDC are known to produce high amounts of IFNα when exposed to enveloped viruses. Since the envelope is derived from the host cell membranes, phosphatidylserine (PS) could to be present in viral envelopes. In fact, for extracellular herpes simplex virus (HSV), the viral membrane was shown to contain a 3-fold higher concentration of PS compared to the host nuclear membrane (van Genderen et al., *Virology* 200(2):831-6, 1994). PS was one of the first molecules described as being recognized by CXCL16 (Shimaoka et al., *J Biol. Chem.* 275(52):40663-6, 2000). Therefore, PS that is expressed on viral envelopes could be recognized by transmembrane CXCL16 on pDC, thereby facilitating virus internalization and subsequent IFNα production.

Example 6

Cancer Treatment

Cancer cells, such as mammary cancer cells 11A-1 (Cancer Res, 55: 3310-7, 1995), Meth A sarcoma cells (DeLeo et al., J Exp Med, 146: 720-34, 1977), or MC-38 (Tan et al., J Natl Cancer Inst (Bethesda), 56: 871-3, 1976) are. Meth A is passaged as an ascitic tumor. Cells are harvested, counted, and washed with PBS before use. Four days after inoculation with 1–2×10$^6$ 11A-1, MC-38, or Meth A cells into six-week-old BALB/c mice (via subcutaneous injection in the left flank), small organized tumor nodules are seen on histological section. Tumors are measured twice weekly in three dimensions with calipers. Growth curves truncate when the first mouse in the respective group dies.

Prior studies have demonstrated the ability to generate p53-specific responses after immunization with modified vaccinia Ankara (MVA) expressing WT murine p53 (MVAp53; Espenschied et al., J Immunol, 170: 3401-7, 2003). Immunized mice develop vigorous p53-specific CTL responses and are able to reject small, established p53-over-expressing Meth A tumors.

In order to accelerate tumor injection, mice are treated with 15 nmol of D ODN (or a non-CpG ODN control) by intraperitoneal (i.p.) injection on days 4, 9, and 14. Groups of mice are administered an agent that induces the expression of CXCL16, such as antagonists of ADAM-10, for example G1254023X or GM6001 in conjunction with the D ODN (see Table 1 for D ODN sequences). On day 5, the mice are immunized i.p. with 5×10$^7$ pfu of MVAp53, 5×10$^7$ pfu of MVApp65, or PBS. The subcutaneous tumors were measured twice weekly in three dimensions with calipers.

Although MVAp53 and D ODN each separately result in minimal attenuation of tumor growth, all animals developed progressively lethal tumors. The combination of D ODN and MVAp53 immunization results in diminished tumor outgrowth. The combination of D ODN, MVAp53 and an antagonist of ADAM-10 significantly decreases tumor growth and/or results in decreased tumor burden.

It will be apparent that the precise details of the methods or compositions described may be varied or modified without departing from the spirit of the described invention. We claim all such modifications and variations that fall within the scope and spirit of the claims below.

The invention claimed is:

1. A method of altering the uptake of a D-type oligodeoxynucleotide by a cell expressing CXCL16, comprising contacting the cell with an effective amount of an agent, wherein the agent is ionomycin, an antibody that specifically binds CXCL16, or a metalloproteinase inhibitor that is an antagonist of ADAM-10; and contacting the cell with the D-type oligodeoxynucleotide, wherein the D-type oligodeoxynucleotide has the sequence $$5'\ X_1X_2X_3\ Pu_1\ Py_2\ CpG\ Pu_3\ Py_4\ X_4X_5X_6(W)_M\ (G)_N\text{-}3' \quad \text{(SEQ ID NO: 21)}$$

wherein the central CpG motif is unmethylated, Pu is a purine nucleotide, Py is a pyrimidine nucleotide, X and W are any nucleotide, M is any integer from 0 to 10, and N is any integer from 4 to 10, and wherein the D-type oligodeoxynucleotide is 18 to 50 nucleotides in length.

2. The method of claim 1, wherein the agent is the metalloproteinase inhibitor that is an antagonist of ADAM-10.

3. The method of claim 2, wherein the agent is GW280264X, G1254023X or GM6001 or a pharmaceutically acceptable salt thereof.

4. The method of claim 1, wherein the agent is GM6001 or a pharmaceutically acceptable salt thereof.

5. The method of claim 1, wherein the agent is the antibody that specifically binds CXCL16.

6. The method of claim 1, wherein the agent is ionomycin.

7. The method of claim 1, wherein $Pu_1\ Py_2$ and $Pu_3\ Py_4$ are self complementary.

8. The method of claim 1, wherein $X_1X_2X_3\ Pu_1\ Py_2$ and $Pu_3\ Py_4\ X_4X_5X_6$ are self complementary.

9. The method of claim 8, wherein the D oligodeoxynucleotide is 18 to 30 nucleotides in length.

10. The method of claim 1, wherein the oligodeoxynucleotide comprises the nucleotide sequence set forth as one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or SEQ ID NO: 17.

11. The method of claim 1, wherein the oligodeoxynucleotide consists of the nucleotide sequence set forth as one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or SEQ ID NO: 17.

12. The method of claim 1, wherein the cell is in vitro.

13. The method of claim 1, wherein the D oliogdoexynucleotide comprises phosphothioate bases.

14. A method of inducing an immune response in a subject, comprising administering to the subject a therapeutically effective amount of a D-type oligodeoxynucleotide and a therapeutically effective amount of an agent, thereby inducing the immune response, wherein the D oligodeoxynucleotide is 18 to 50 nucleotides in length and has the sequence $$5'\ X_1X_2X_3\ Pu_1\ Py_2\ CpG\ Pu_3\ Py_4\ X_4X_5X_6(W)_M\ (G)_N\text{-}3' \quad \text{(SEQ ID NO: 21)}$$

wherein the central CpG motif is unmethylated, Pu is a purine nucleotide, Py is a pyrimidine nucleotide, X and W are any nucleotide, M is any integer from 0 to 10, and N is any integer from 4 to 10, and wherein the agent is a metalloproteinase inhibitor that is an antagonist of ADAM-10.

15. The method of claim 14, metalloproteinase inhibitor is GW280264X, G1254023X or GM6001.

16. The method of claim 14, wherein $Pu_1\ Py_2$ and $Pu_3\ Py_4$ are self complementary.

17. The method of claim 14, wherein $X_1X_2X_3\ Pu_1\ Py_2$ and $Pu_3\ Py_4\ X_4X_5X_6$ are self complementary.

18. The method of claim 17, wherein the D oligodeoxynucleotide is 18 to 30 nucleotides in length.

19. The method of claim 14, wherein the oligodeoxynucleotide comprises the nucleotide sequence set forth as one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or SEQ ID NO: 17.

20. The method of claim 14, wherein the oligodeoxynucleotide consists of the nucleotide sequence set forth as one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or SEQ ID NO: 17.

21. The method of claim 14, wherein the D oliogdoexynucleotide comprises phosphothioate bases.

22. The method of claim 14, further comprising administering an anti-infectious agent to the subject.

23. The method of claim 14, further comprising administering a vaccine against an infectious agent to the subject, thereby inducing an immune response to the infectious agent in the subject.

24. The method of claim 14, wherein the oligodeoxynucleotide comprises the nucleotide sequence set forth as SEQ ID NO: 1.

25. The method of claim 14, wherein the oligodeoxynucleotide consists of the nucleotide sequence set forth as SEQ ID NO: 1.

26. The method of claim 14, wherein the agent is GM6001 or a pharmaceutically acceptable salt thereof.

* * * * *